US008796438B2

(12) United States Patent
Morin

(10) Patent No.: US 8,796,438 B2
(45) Date of Patent: Aug. 5, 2014

(54) NUCLEIC ACIDS ENCODING INACTIVE VARIANTS OF HUMAN TELOMERASE

(75) Inventor: Gregg B. Morin, Davis, CA (US)

(73) Assignees: Geron Corporation, Menlo Park, CA (US); The Regents of the University of Colorado, Boulder, CO (US)

( * ) Notice: Subject to any disclaimer, the term of this patent is extended or adjusted under 35 U.S.C. 154(b) by 2 days.

(21) Appl. No.: 11/504,402

(22) Filed: Aug. 14, 2006

(65) Prior Publication Data

US 2006/0275267 A1 Dec. 7, 2006

Related U.S. Application Data

(60) Division of application No. 09/990,080, filed on Nov. 21, 2001, now Pat. No. 7,091,021, which is a continuation of application No. 09/128,354, filed on Aug. 3, 1998, now Pat. No. 6,337,200, which is a continuation-in-part of application No. 09/052,864, filed on Mar. 31, 1998, now abandoned.

(51) Int. Cl.
*A61K 38/00* (2006.01)

(52) U.S. Cl.
USPC ..... 536/23.2; 536/23.1; 435/69.1; 435/320.1; 435/6

(58) Field of Classification Search
None
See application file for complete search history.

(56) References Cited

U.S. PATENT DOCUMENTS

| | | | |
|---|---|---|---|
| 3,817,837 A | 6/1974 | Tanenholtz et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,554,101 A | 11/1985 | Hopp |
| 4,683,195 A | 7/1987 | Mullis et al. |
| 4,683,202 A | 7/1987 | Mullis |
| 4,816,567 A | 3/1989 | Cabilly et al. |
| 4,889,806 A | 12/1989 | Olson et al. |
| 4,965,188 A | 10/1990 | Mullis et al. |
| 5,001,225 A | 3/1991 | Taylor |
| 5,075,227 A | 12/1991 | Hagen |
| 5,489,508 A | 2/1996 | West et al. |
| 5,583,016 A | 12/1996 | Villeponteau et al. |
| 5,597,697 A | 1/1997 | Diamond |
| 5,639,613 A | 6/1997 | Shay et al. |
| 5,698,686 A | 12/1997 | Gottschling et al. |
| 5,747,317 A | 5/1998 | Cao |
| 5,770,422 A | 6/1998 | Collins |
| 5,853,719 A | 12/1998 | Nair et al. |
| 5,917,025 A | 6/1999 | Collins |
| 5,919,656 A | 7/1999 | Harrington et al. |
| 5,919,676 A | 7/1999 | Graham et al. |
| 6,093,809 A | 7/2000 | Cech et al. |
| 6,120,764 A | 9/2000 | Graham et al. |
| 6,140,087 A | 10/2000 | Graham et al. |
| 6,166,178 A | 12/2000 | Cech et al. |
| 6,258,535 B1 | 7/2001 | Villeponteau et al. |
| 6,261,556 B1 | 7/2001 | Weinrich et al. |
| 6,261,836 B1 | 7/2001 | Cech et al. |
| 6,306,388 B1 | 10/2001 | Nair et al. |
| 6,309,867 B1 | 10/2001 | Cech et al. |
| 6,337,200 B1 | 1/2002 | Morin |
| 6,387,701 B1 | 5/2002 | Nair et al. |
| 6,440,735 B1 | 8/2002 | Gaeta |
| 6,444,650 B1 | 9/2002 | Cech et al. |
| 6,475,789 B1 | 11/2002 | Cech et al. |
| 6,517,834 B1 | 2/2003 | Weinrich et al. |
| 6,545,133 B1 | 4/2003 | Weinrich et al. |
| 6,608,188 B1 | 8/2003 | Tsuchiya et al. |
| 6,610,839 B1 | 8/2003 | Morin et al. |
| 6,617,110 B1 | 9/2003 | Cech et al. |
| 6,627,619 B2 | 9/2003 | Cech et al. |
| 6,767,719 B1 | 7/2004 | Morin et al. |
| 6,777,203 B1 | 8/2004 | Morin et al. |
| 6,787,133 B2 | 9/2004 | Weinrich et al. |
| 6,808,880 B2 | 10/2004 | Cech et al. |
| 6,846,662 B1 | 1/2005 | Kilian et al. |
| 6,916,642 B1 | 7/2005 | Kilian et al. |
| 6,921,664 B2 | 7/2005 | Cech et al. |
| 6,927,285 B2 | 8/2005 | Cech et al. |
| 7,005,262 B2 | 2/2006 | Cech et al. |
| 7,056,513 B2 | 6/2006 | Cech et al. |
| 7,091,021 B2 | 8/2006 | Morin |
| 7,195,911 B2 | 3/2007 | Cech et al. |
| 7,262,174 B2 | 8/2007 | Jiang et al. |
| 7,262,288 B1 * | 8/2007 | Cech et al. ................... 536/23.5 |

(Continued)

FOREIGN PATENT DOCUMENTS

| | | |
|---|---|---|
| WO | WO 98/07838 | 2/1998 |
| WO | WO 98/21343 | 5/1998 |

(Continued)

OTHER PUBLICATIONS

Adams, M. et al., "Initial Assessment of Human Gene Diversity and Expression Patterns Based Upon 83 Million Nucleotides of cDNA Sequence," *Nature* 377(6574S):3-174 (Sep. 28, 1995).
Adamson, D. et al., "Significant telomere shortening in childhood leukemia," *Cancer Genet. Cytogenet* 61:204-6 (1992).
Autexier, C. & Greider, C., "Telomerase and cancer: Revisiting the telomere hypothesis," *Trends Biochem. Sci.* 10(21):387-91 (1996).
Autexier, C. et al., "Reconstitution of human telomerase activity and identification of a minimal functional region of the human telomerase RNA," *EMBO J.* 15:5928-35 (1996).
Auxexier, C. & Greider, C., "Functional reconstitution of wild-type and mutant *Tetrahymena* telomerase," *Genes Dev.* 8:563-75 (1994).
Avilion, A., "Characterization and expression of human telomerase," Dissertation, State University of New York at Stonybrook (May 1995) 263 pages.

(Continued)

*Primary Examiner* — Hope Robinson
(74) *Attorney, Agent, or Firm* — Leslie A. Mooi

(57) ABSTRACT

The invention provides compositions and methods related to human telomerase reverse transcriptase (hTRT), the catalytic protein subunit of human telomerase. Catalytically inactive variants comprising deletions or other mutations are provided.

9 Claims, 2 Drawing Sheets

(56) References Cited

U.S. PATENT DOCUMENTS

| | | | |
|---|---|---|---|
| 7,285,639 | B2 | 10/2007 | Cech et al. |
| 7,294,708 | B2 | 11/2007 | Huang et al. |
| 7,297,488 | B2 | 11/2007 | Cech et al. |
| 7,378,244 | B2 | 5/2008 | Morin et al. |
| 7,413,864 | B2 | 8/2008 | Cech et al. |
| 7,517,971 | B1 | 4/2009 | Cech et al. |
| 7,560,437 | B2 | 7/2009 | Cech et al. |
| 7,585,622 | B1 | 9/2009 | Cech et al. |
| 2003/0044394 | A1 | 3/2003 | Gaeta |
| 2003/0096344 | A1 | 5/2003 | Cech et al. |
| 2003/0204069 | A1 | 10/2003 | Morin et al. |
| 2004/0072787 | A1 | 4/2004 | Morin et al. |
| 2004/0242529 | A1 | 12/2004 | Cech et al. |
| 2004/0247613 | A1 | 12/2004 | Cech et al. |
| 2004/0253701 | A1 | 12/2004 | Morin et al. |
| 2005/0013825 | A1 | 1/2005 | Cech et al. |
| 2006/0040307 | A1 | 2/2006 | Cech et al. |
| 2006/0204483 | A1 | 9/2006 | Gaeta |
| 2008/0279871 | A1 | 11/2008 | Cech et al. |

FOREIGN PATENT DOCUMENTS

| | | |
|---|---|---|
| WO | WO 98/37181 | 8/1998 |
| WO | WO 99/01560 | 1/1999 |
| WO | WO-2005/044179 | 5/2005 |
| WO | WO-2005/000245 | 6/2005 |

OTHER PUBLICATIONS

Barinaga, M., "The telomerase picture fills in," *Science* 276:528-9 (Apr. 25, 1997).
Bradford, M., "A rapid and sensitive method for the quantitation of microgram quantities of protein utilizing the principle of protein-dye binding," *Anal. Biochem.* 72:248-54 (1976).
Calvio, C. et al., "Identification of hnRNP P2 as TLS/FUS using electrospray mass spectrometry," *RNA* 1:724-33 (1995).
Campbell, K. & Wilmut, I., "Totipotency or multipotentiality of cultured cells: applications and progress," *Theriogenology* 47(1):63-72 (Jan. 1997).
Chan, C. & Tye, B., "Organization of DNA sequences and replication origins at yeast telomeres," *Cell* 33:(2):563-73 (1983).
Colbère-Garapin, F. et al., "A new dominant hybrid selective marker for higher eukaryotic cells," *J. Mol. Biol.* 150(1):1-14 (1981).
Collins, K. et al., "Purification of Tetrahymena telomerase and cloning of genes encoding the two protein components of the enzyme," *Cell* 81:677-86 (1995).
Collins, K., "Structure and function of telomerase," *Curr. Opin. Cell Biol.* 8:374-80 (1996).
Conrad, M. et al., "RAP1 protein interacts with yeast telomeres in vivo: Overproduction alters telomere structure and decreases chromosome stability," *Cell* 63:739-50 (1990).
Counter, C. et al., "Telomerase activity in human ovarian carcinoma," *Proc. Natl. Acad. Sci USA* 91:2900-4 (Apr. 1994).
Counter, C. et al., "Telomerase activity in normal leukocytes and in hematologic malignancies," *Blood* 85(9):2315-20 (May 1, 1995).
Duplàa, C. et al., "Quantitative analysis of polymerase chain reaction products using biotinylated dUTP incorporation," *Anal. Biochem.* 212:229-36 (1993).
Fang, G. et al., "*Oxytricha* telomere-binding protein: separable DNA-binding and dimerization domains of the α-subunit," *Genes Dev.* 7:870-2 (1993).
Flavell, R. & Mathias, R., "Prospects for transforming monocot crop plants," *Nature* 307:108-9 (Jan. 1984).
GenBank Accession No. A46242; (Sep. 21, 1993).
GenBank Accession No. AA281296; (Apr. 2, 1997).
GenBank Accession No. AA299878; (Apr. 18, 1997).
GenBank Accession No. AA311750; (Apr. 19, 1997).
GenBank Accession No. L38903; (Jan. 30, 1995).
GenBank Accession No. Q06163; (Nov. 1, 1995).
GenBank Accession No. S39696; (Oct. 7, 1994).
GenBank Accession No. S53396; (May 5, 1995).
GenBank Accession No. U95964; (May 5, 1997).
GenBank Accession No. W70315; (Jun. 19, 1996).
Gilley, D. et al., "Altering specific telomerase RNA template residues affects active site function," *Genes Develop.* 9:2214-26 (1995).
Goodman, R. et al., "Gene transfer in crop improvement," *Science* 236:48-54 (Apr. 3, 1987).
Healy, K., "Telomere dynamics and telomerase activation in tumor progression: prospects for prognosis and therapy," *Oncol. Res.* 7:121-30 (1995).
Henderson, C., "Cancer genetics gene regulates telomerase resulting in death of cancer cells," *Gene Therapy Weekly* (Sep. 11, 1995) 2 pages.
Henderson, E. & Blackburn, E., "An overhanging 3' terminus is a conserved feature of telomeres," *Mol Cell. Biol.* 9(1):345-8 (1989).
Hornsby, P., "Adrenocortical cells immortalized by telomerase: Potential use for ex Vivo gene therapy," *J. Anti-Aging Med.* 3(4):411-7 (2000).
Jähne, A. et al., "Genetic engineering of cereal crop plants: A review," *Euphytica* 85:35-44 (1995).
Johnson, P. et al., "Expression of wild-type p53 is not compatible with continued growth of p53-negative tumor cells," *Mol. Cell. Biol.* 11(1):1-11 (1991).
Jolliffe, L., "Humanized antibodies: enhancing therapeutic utility through antibody engineering," *Int. Rev. Immunol.* 10:241-50 (1993).
Klobutcher, L. et al., "All gene-sized DNA molecules in four species of hypotrichs have the same terminal sequence and an unusual 3' terminus," *Proc. Natl. Acad. Sci. USA* 78:3015-9 (1981).
Lewis, A. & Crowe, J., "Generation of humanized monoclonal antibodies by 'best fit' framework selection and recombinant polymerase chain reaction," *Year Immunol.* 7:110-8 (1993).
Lingner, J. & Cech, T., "Purification of telomerase from *Euplotes adeiculatus*: requirement of a primer 3' overhang," *Proc. Natl. Acad. Sci. USA* 93:10712-7 (1996).
Lingner, J. et al., "Telomerase RNAs of different ciliates have a common secondary structure and a permuted template," *Genes Dev.* 8:1984-98 (1994).
Lustig, A. & Petes, T., "Identification of yeast mutants with altered telomere structure," *Proc. Natl. Acad. Sci. USA* 83:1398-402 (Mar. 1986).
Maddox, D. et al., "Elevated serum levels in human pregnancy of a molecule immunochemically similar to eosinophil granule major basic protein," *J. Exp. Med.* 158:1211-26 (Oct. 1983).
Nakayama, J. et al., "TLP1: a gene encoding a protein component of mammalian telomerase is a novel member of WD repeats family," *Cell* 88:875-84 (1997).
Nakayama, J. et al., "Cloning of a Candidate cDNA Encoding a Proteinaceous Component of Mammalian Telomerase," *Molecular Biology Cell Abstracts, Supp.* 7, pp. 875-884, 286a, Section 1664 (1996).
Orlandi, R. et al., "Cloning immunoglobulin variable domains for expression by the polymerase chain reaction," *Proc. Natl. Acad. Sci. USA* 86:3833-7 (May 1989).
Ostler E. et al., "Telomerase and the Cellular Lifespan: Implications for the Aging Process," *J. Pediatr. Endocrinol. Metab.* 13(Suppl. 6):1467-76 (2000).
Paszkowski, J. et al., "Direct gene transfer to plants," *EMBO J.* 3(12):2717-22 (1984).
Prescott, D., "The DNA of ciliated protozoa," *Microbiol. Rev.* 58(2):233-67 (Jun. 1994).
Raymond, E. et al., "Agents that target telomerase and telomeres," *Curr. Opin. Biotechnol.* 7:583-91(1996).
Rhyu, M., "Telomeres, telomerase, and immortality" *J. Natl. Cancer Inst.* 87(12):884-94 (Jun. 1995).
Sambrook, J. et al., Chapter 16: "Expression of Cloned Genes in Cultured Mammalian Cells," *Molecular Cloning, A Laboratory Manual*, Cold Spring Harbor Laboratory Press, Plainview, NY (1989).
Sambrook, J. et al., Chapter 17, "Expression of Cloned Genes in *Escherichia coli*," *Molecular Cloning, A Laboratory Manual*, Cold Spring Harbor Laboratory Press, Plainview, NY (1989).
Sandell, L. et al., "Transcription of yeast telomere alleviates telomere position effect without affecting chromosome stability," *Proc. Natl. Acad. Sci. USA* 91:12061-5 (1994).

(56) References Cited

OTHER PUBLICATIONS

Sanger, F. et al., "DNA sequencing with chain-terminating inhibitors," *Proc. Natl. Acad. Sci. USA* 74(12):5463-7 (1977).
Shampay, J. & Blackburn, E., "Generation of telomere-length heterogeneity in *Saccharomyces cerevisiae*," *Proc. Natl. Acad. Sci. USA* 85:534-8 (Jan. 1988).
Sheen, F. & Levis, R., "Transposition of the LINE-like retrotransposon TART to *Drosophila* chromosome termini," *Proc. Natl. Acad. Sci. USA* 91:12510-4 (Dec. 1994).
Singer, M., "Unusual reverse transcriptases," *J. Biol. Chem.* 270(42):24623-6 (1995).
Takano, M. & Ishikawa, F., The Adjustment Foundation of Science and Technology Promotion News, vol. 160, pp. 0-6 (Jul. 11, 1997). Japanese language document.
Wellinger, R. et al., "Origin activation and formation of single-strand TG1-3 tails occur sequentially in late S phase on a yeast linear plasmid," *Mol. Cell. Biol.* 13(7):4057-65 (Jul. 1993).
Wigler, M. et al., "Transformation of mammalian cells with an amplifiable dominant-acting gene," *Proc. Natl. Acad. Sci. USA* 77(6):3567-70 (1980).
Wirth, U. et al., "Immediate-early RNA 2.9 and early RNA 2.6 of bovine herpesvirus 1 are 3' coterminal and encode of putative zinc finger transactivator protein," *J. Virol.* 66(5):2763-72 (1992).
Wright, J. et al., "*Saccharomyces* telomeres assume a non-nucleosomal chromatin structure," *Genes Dev.* 6:197-210 (1992).
Zahler, A. & Prescott, D., "Telomere terminal transferase activity in the hypotrichous ciliate *Oxytricha nova* and a model for replication of the ends of linear DNA molecules," *Nucl. Acids Res.* 16:6953-72 (1988).
Zaug, A. et al., "Method for determining RNA 3' ends and application to human telomerase RNA," *Nucl. Acids Res.* 24(3):532-3 (1996).
Bachand et al., Functional Regions of Human Telomerse Reverse Transcriptase and Human Telomerase RNA Required for Telomerase Activity and RNA-Protein Interactions, Mol. and Cellular Biol. 21:1888 (2001).
Bodnar et al., Extension of Life-span by Induction of Telomerase into Normal Human Cells, Science 279:349 (1998).
Bryan et al., A Mutant of *Tetrahymena* Telomerase Reverse Transcriptase with Increased Processivity, J. Biol. Chem. 275:24199 (2000).
Bryan et al., Telomerase RNA Bound by Protein Notifs Specific to Telomerase Reverse Transcriptase, Molecular Cell 6:493 (2000).
Bryan et al., Telomerase reverse transcriptase genes identified in Tetrahymena thermophila and Oxytricha trifallax, Proc. Natl. Acad. Sci. USA 95:8479 (1998).
Colgin et al., The hTERTapha splice variant is a dominant negative inhibitor of telomerase activity, Neoplasia 2:426 (2000).
Farmery et al., Major Histocompatability Class I Folding, Assembly, and Degradation: A Paradigm for Two-Stage Quality Control in the Endoplasmic Reticulum, Progress in Nucleic Acid Res. 67:235 (2001).
Freidman et al., Essential functions of amino-terminal domains in the yeast telomerase catalytic subunit revealed by selection for variable mutants, Genes & Dev. 13:2863 (1999).
Haering et al., Analysis of telomerase catalytic subunit mutants in vivo and in vitro in *Schizosaccharomyces pombe*, PNAS 97:6367 (2000).
Hahn et al., Inhibition of telomerase limits the growth of human cancer cells, Nature Medicine 5:1164 (1999).
Harrington et al., Human telomerase contians evolutionarily consderved catalytic and structural subunits, Genes Dev. 11:3109 (1997).
Kilian et al., Isolation of a Candidate Human Telomerase Catalytic Subunit Gene, Which Reveals Complex Splicing Patterns in Different Cell Types, Hum. Mol. Genet. 6:2011 (1997).
Lai et al., RNA Binding Domain of Telomerase Reverse Transcriptase, Mol. and Cellular Biol. 21:990 (2000).
Lingner et al., Reverse Transcriptase Motifs in the Catalytic Subunit of Telomerase, Science 276:561 (1997).

Morin, The Implications of Telomerase Biochemistry for Human Disease, Eur. J. Biol. Chem. 33:750(1998).
Myerson et al., hEST2, the Putative Human Telomerase Catalytic Subunit Gene, Is Up-Regulated in Tumor Cells and during Immortalization, Cell 90:785 (1997).
Nakamura et al., Telomerase Catalytic Subunit Homologs from Fission Yeast and Human, Science 277:955 (1997).
Perez et al., Human formyl peptide receptor ligand binding domain(s). Studies using an improved mutagenesis/expression vector reveal a novel mechanism for the regulation of receptor occupancy, J. Biol. Chem. 269:22485 (1994).
Solheim et al., Class I MHC molecules: assembly and antigen presentation, Immun. Reviews 172:11 (1999).
Weinrich et al., Reconstitution of Human Telomerase with the Template RNA Component hTR and the Catalytic Protein Subunit hTRT, Nat. Genet. 17:498 (1997).
Xia et al., Identificationof Funtionally Important Domains in the N-Terminal Region of Telomerase Reverse Transcriptase, Mol. and Cellular Biol. 20:5196 (2000).
Zakharova et al., Structural Constraints in the HIV-1 Reverse Transcriptase-PrimerfTemplate Complex for the Initiation of DNA Synthesis from Primer tRNA$^{Lys3}$, Biochem. 37:13343 (1998).
Bitter, G. et al., "Expression and secretion vectors for yeast," *Meth. Enzymol.* 153:516-44 (1987).
Gottschling, D. & Cech, T., "Chromatin structure of the molecular ends of Oxytricha mononuclear DNA: Phased nucleosomes and a telomeric complex," *Cell* 38:501-10 (Sep. 1984).
Gottschling. D. & Zakian, V., "Telomere proteins: specific recognition and protection of the natural termini of Oxytricha macronuclear DNA," *Cell* 47:195-205 (1986).
Greenwood, S. et al., "Phylogenetic relationships within the class oligohymenophorea, phylum ciliophora, inferred from the complete small subunit rRNA gene sequences of *Colpidium campylum, Glaucoma chattoni*, and *Opisthonecta henneguyi*," *J. Mol. Evol.* 33:163-74 (1991).
Greider, C. & Blackburn, E., "Identification of a specific telomere terminal transferase activity in Tetrahymena extracts," *Cell* 43:405-13 (Dec. 1985).
Holzmann, K. et al., "Telomeric associations and loss of telomeric DNA repeats in renal tumors," *Genes Chromosomes Cancer* 6:178-81 (1993).
Hudson, T. et al., "An STS-based map of the human genome," *Science* 270:1945-54 (1995).
Huse, W. et al., "Generation of a large combinatorial library of the immunoglobulin repertoire in phage lambda," *Science* 246:1275-81 (1989).
Kinsella, T. & Nolan, G., "Episomal vectors rapidly and stably produce high-titer recombinant retrovirus," *Hum. Gene Ther.* 7:1405-13 (1996).
Kipling, D. & Cooke, H., "Hypervariable ultra-long telomeres in mice," *Nature* 347:400-2 (1990).
Kiwaki, K. et al., "Correction of ornithine transcarbamylase deficiency in adult spf$^{ash}$ mice and in OTC-deficient human hepatocytes with recombinant adenoviruses bearing the CAG promoter," *Hum. Gene Ther.* 7:821-30 (1996).
Köhler, G. & Milstein, C., "Continuous cultures of fused cells secreting antibody of predefined specificity," *Nature* 256:495-7 (1975).
Lamond, A. et al., "Probing the structure and function of U2 snRNP with antisense oligonucleotides made of 2'-OMe RNA," *Cell* 58:383-90 (Jul. 1989).
Lingner, J. et al., "Telomerase and DNA end replication: No longer a lagging strand problem?" *Science* 269:1533-4 (1995).
Lowy, I. et al., "Isolation of transforming DNA: Cloning the hamster aprt gene," *Cell* 22:817-23 (Dec. 1980).
Lundblad, V. & Blackburn, E., "RNA-Dependent Polymerase Motifs in EST1: Tentative Identificatioin of a Protein Component of an Essential Yeast Telomerase," *Cell* 60:529-30 (Feb. 23, 1990).
Lustig, A., "The identification of telomerase subunits: catalysing telomere research," *Trends in Cell Biology* 7:299-302 (Aug. 1997).
Makarov, V. et al., "Nucleosomal organization of telomere-specific chromatin in rat," *Cell* 73:775-87 (1993).

(56) References Cited

OTHER PUBLICATIONS

McEachern, M. & Blackburn, E., "Runaway telomere elongation caused by telomerase RNA gene mutations," *Nature* 376:403-9 (Aug. 1995).
Merrifield, R., "Solid phase peptide synthesis. I. The synthesis of a tetrapeptide," *J. Am. Chem. Soc.* 85:2149-54 (Jul. 1963).
Olovnikov, A., "A Theory of marginotomy: The incomplete copying of template margin in enzymic synthesis of polynucleotides and biological significance of the phenomenon," *J. Theor. Biol.* 41:181-90 (1973).
Potrykus, I. et al., "Direct gene transfer to cells of a graminaceous monocot," *Mol. Gen. Genet.* 199:183-8 (1985).
Roberge, J. et al., "A strategy for a convergent synthesis of N-linked glycopeptides on a solid support," *Science* 269:202-4 (1995).
Romero, D. & Blackburn, E., "A conserved secondary structure for telomerase RNA," *Cell* 67:343-53 (Oct. 1991).
Singer, M. & Gottschling, D., "TLC1: Template RNA component of *Saccharomyces cerevisiae* telomerase," *Science* 266:404-9 (Oct. 1994).
Swanton, M. et al., "Arrangement of coding and non-coding sequences in the DNA molecules coding for rRNAs in *Oxytricha sp.*," *Chromosoma* 77:203-15 (1980).
Tait, J. et al., "Structure and polymorphisms of the human annexin III (ANX3) gene," *Genomics* 18(1):79-86 (1993).
Wellinger, R. et al., "*Saccharomyces* telomeres acquire single-strand TG1-3 tails late in S phase," *Cell* 72:51-60 (1993).
Wigler, M. et al., "Transfer of purified herpes virus thymidine kinase gene to cultured mouse cells," *Cell* 11:223-32 (1977).
Winter, G. & Milstein, C., "Man-made antibodies," *Nature* 349:293-9 (Jan. 1991).
Zakian, V., "Telomeres: beginning to understand the end," *Science* 270:1601-7 (1995).
"Linking telomerase and tumors," *The Genesis Report-Dx* vol. 4 No. 6, Genesis Group Associates, Inc. (May 1, 1995) Accession No. 95:91307 NLDB, 2 pages.
Office Action in U.S. Appl. No. 09/721,477 dated May 7, 2008.
Alberts, B. et al., *Molecular Biology of the Cell*, Garland Publishing, New York, p. 326, Fig. 7-73 (Jul. 20, 1995).
Anderson, M. & Young, B. "Quantitative Filter Hybridisation," *Nucleic Acid Hybridization—A Practical Approach*, B.D. Hames and S.J. Higgins (Eds.), IRL Press, Washington, D.C., pp. 73-111 (1985).
Caruthers, M. et al., "New chemical methods for synthesizing polynucleotides," *Nucleic Acids Symp. Series* 7:215-223 (1980).
Cole, S. et al., "The EBV-hybridoma technique and its application to human lung cancer," *Monoclonal Antibodies and Cancer Therapy*, pp. 77-96, Alan R. Liss Inc., New York (1985).
Coombs, J., *Dictionary of Biotechnology*, pp. 101-102, 283, 301, 332, Stockton Press, New York (1994).
Creighton, T., *Proteins: Structure and Molecular Principles*, W.H. Freeman and Co., New York, pp. 1-60 (1984).
Dieffenbach, C. & Dveksler, G. (Eds.), *PCR Primer, A Laboratory Manual*, Cold Spring Harbor Laboratory Press, Plainview, New Yoek, Table of Contents (1995).
Genome Issue of *Science* 265:1981-2144 (Sep. 30, 1994).
Glaser, P. et al., "*Bacillus subtilis* genome project: cloning and sequencing of the 97 kb region from 325 ° to 333 °," *Mol. Microbiol.* 10(2):371-84 (1993).
Greider, C., "Telomere length regulation," *Annu. Rev. Biochem.* 65:337-65 (1996).
Hiyama, E. et al., "Correlating telomerase activity levels with human neuoblastoma outcomes," *Nature Medicine* 1(3):249-55 (Mar. 3, 1995).
Horn, T. et al., "Synthesis of oligonucleotides on cellulose. Part II: design and synthetic strategy to the synthesis of 22 oligodeoxynucleotides coding for gastric inhibitory polypeptide (GIP)," *Nucl. Acids Symp. Ser.* 7:225-32 (1980).
Kimmel, A. & Berger, S., "Preparation of cDNA and the generation of cDNA libraries: overview," *Meth. Enzymol.* 152:307-16 (1987).
Kozbor, D. & Roder, J., "The production of monoclonal antibodies from human lymphocytes," *Immunol. Today* 4:72-9 (1983).

Lamond, A. & Sproat, B., "Isolation and Characterization of Ribonucleoprotein Complexes,", *RNA Processing, A Practical Approach*, vol. 1, pp. 103-140, Eds. Higgins & Hames, Oxford University Press, New York (1994).
Melby, P. et al., "Quantitative measurement of human cytokine gene expression by polymerase chain reaction," *J. Immunol. Meth.* 159:235-44 (1993).
Murray, L., *McGraw Hill Yearbook of Science and Technology*, pp. 189-196, McGraw Hill, New York (1992).
Nielsen, P. et al., "Peptide nucleic acids (PNAs): Potential antisense and anti-gene agents," *Anticancer Drug Des.* 8:53-63 (1993).
Oka, Y. et al., "Inverted terminal repeat sequence in the macronuclear DNA of *Stylonychia pustulata*," *Gene* 10:301-6 (1980).
Price, C., "Fluorescence in situ hybridization," *Blood Reviews* 7:127-34 (1993).
Rhodes, C. et al., "Transformation of maize by electroporation of embryos," *Meth. Mol. Biol.* 55:121-31 (1995).
Sambrook, J. et al., Chapter 8, "Construction and Analysis of CDNA Libraries," *Molecular Cloning, A Laboratory Manual*, Cold Spring Harbor Laboratory Press, Plainview, NY, pp. 8.1-8.86 (1989).
Scharf, K. et al., "Heat stress promoters and transcription factors," *Results Probl. Cell Differ.* 20:125-62 (1994).
Schwartz, H. et al., "Telomere reduction in giant cell tumor of bone and with aging," *Cancer Genet. Cytogenet.* 71:132-8 (1993).
Smith, J. & Yeh, G., "Telomere reduction in endometrial adenocarcinoma," *Am. J. Obstet. Gynecol.* 167(6):1883-7 (Dec. 1992).
Tani, K. et al., "Transduction of LacZ gene into leukemia cells using viral vectors of retrovirus and adenovirus," *Leukemia* 9(Suppl. 1):S64-5 (1995).
Verma, R. & Babu, A., *Human Chromosomes: Manual of Basic Techniquies*, Pergamon Press, New York, Table of Contents (1989).
Watson, J., "Origin of concatemeric T7 DNA," *Nature New Biol.* 239:197-201 (Oct. 1972).
Whitehead Institute/MIT Center for Genome Research, Genetic Map of the Mouse, Database Release 10, 4 pages (Apr. 28, 1995).
Winter, G. & Harris, W., "Humanized antibodies," *Trends Pharmacol. Sci.* 14:139-43 (May 1993).
Zaug, A. et al., "Catalysis of RNA cleavage by ribozyme derived from the group I intron of *Anabaena* Pre-tRNA$^{Leu}$," *Biochemistry* 33:14935-47 (1994).
*NCBI Reference No. NM_011210.3, Mus musculus* www.ncbi.nlm.nih.gov/nuccore/162417964 (Jun. 2, 2009).
Genbank Accession No. W33708 Mus musculus (May 16, 1996), 2 pages.
Ausubel, F. et al., *Current Protocols in Molecular Biology*, John Wiley & Sons, New York, Table of Contents 1996.
Hampton, R. et al., *Serological Methods for Detection and Identification of Viral and Bacterial Plant Pathogens: A Laboratory Manual*, APS Press, St. Paul MN 1990 , pp. 33-86, 179-286.
Harlow et al., *Antibodies: A Laboratory Manual*, CSHL Press, Chapter 5, 1988, p. 76.
Hathcock, K. et al., "Expression of variable exon A-, B-, and C-specific CD45 determinants on peripheral and thymic T cell populations", *J. Immunol.* 148(1) 1992 , pp. 19-28.
Janeway, C. et al., *Immunobiology: The Immune System in Health and Disease*, 3rd Ed., Garland Publishing, Inc., New York,1997, p. G1.
Okada, Y. et al., "Expression of information and control in higher plant", *Japanese Molecular Biology Association Edition, Development of Molecular Biology 13, Maruzen Corp.* Feb. 10, 1990 , pp. 262-263.
Saga, Y. et al., "Organization of the Ly-5 gene," *Mol. Cell. Biol.* 8(11) 1988 , pp. 4889-4895.
Weldon, S. et al., "Monoclonal antibodies as probes for functional domains in cAMP-dependent protein kinase II", *J. Biol. Chem.* 260(7) (1985), pp. 4203-4209.
Weldon, S. et al., "Monoclonal antibodies as structural probes of surface residues in the regulatory subunit of cAMP-dependent protein kinase II from porcine heart", *J. Biol. Chem.* 258(2) (1983), pp. 1129-1135.

(56) References Cited

OTHER PUBLICATIONS

Liu, C. et al., "The telomerase reverse Transcriptase (hTERT) gene is a direct target of the histone methyltransferase SMYD3", *Cancer Res.* 67, (2007), pp. 2626-2631.

Peng, H. et al., "Multiple PCR analyses on trace amounts of DNA extracted from fresh and paraffin wax embedded tissues after random hexamer primer PCR amplification", *J. Clin. Pathol.* 47. (1994), pp. 605-608.

Abaza, M. et al., "Effects of amino acid substitutions outside an antigenic site on protein binding to monoclonal antibodies of predetermined specificity obtained by peptide immunization: demonstration with region 94-100 (antigenic site 3) of myoglobin," *J. Prot. Chem.* 11(5):433-44 (1992).

Adaptive definition, www.answers.com/topic/adaptive, 1 page (2007).

Alberts, B. et al., *Molecular Biology of the Cell*, Newton Press Ltd., pp. 66, 85, 347 (Jul. 20, 1995).

Anderson, W. French, "Human Gene Therapy," *Nature* 392(Suppl.):25-30 (Apr. 30, 1998).

Ayyoub, M. et al., "Lack of tumor recognition by hTERT peptide 540-548-specific CD8+ T cells from melanoma patients reveals inefficient antigen processing," *Eur. J. immunol.* 31:2642-51 (2001).

Bandyopadhyay, D. et al., "The human melanocyte: a model system to study the complexity of cellular aging and transformation in non-fibroblastic cells," *Exp. Gerontol.* 36:1265-75 (2001).

Beasley, E. et al., "Statistical refinement of primer design parameters," *PCR Applications*, Innis et al., Eds., Academic Press, San Diego, pp. 55-71 (1999).

Bellone, M. et al., "In vitro priming of cytotoxic T lymphocytes against poorly immunogenic epitopes by engineered antigen-presenting cells," *Eur. J. Immunol.* 24:2691-8 (1994).

Bellone, M. et al., "Rejection of a nonimmunogenic melanoma by vaccination with natural melanoma peptides on engineered antigen-presenting cells," *J. Immunol.* 158:783-9 (1997).

Benedict, C. et al., "The long isoform of terminal deoxynucleotidyl transferase enters the nucleus and, rather than catalyzing nontemplated nucleotide addition, modulates the catalytic activity of the short isoform," *J. Exp. Med.* 193(1):89-99 (2001).

Biessmann, H. et al., "Addition of telomere-associated HeT DNA sequences 'heals' broken chromosome ends in *Drosophila*," *Cell* 61:663-73 (1990).

Blackburn, E. & Chiou, S., "Non-nucleosomal packaging of a tandemly repeated DNA sequence at termini of extrachromosomal DNA coding for rRNA in *Tetrahymena*," *Proc. Natl. Acad. Sci. USA* 78(4):2263-7(1981).

Blackburn, E. & Gall, J. "A tandemly repeated sequence at the termini of the extrachromosomal ribosomal RNA genes in *Tetrahymena*," *J. Mol. Biol.* 120(1):33-53 (1978).

Blackburn, E., "Telomerases," *Annu. Rev. Biochem.* 61:113-29 (1992).

Boczkowski, D. et al., "Dendritic cells pulsed with RNA are potent antigen-presenting cells in vitro and in vivo," *J. Exp. Med.* 184:465-72 (1996).

Bowie, J. et al., "Deciphering the message in protein sequences: tolerance to amino acid substitutions," *Science* 257:1306-10 (1990).

Bramson, J. et al., "The use of adenoviral vectors for gene therapy and gene transfer in vivo," *Curr. Opin. Biotechnol.* 6:590-5 (1995).

Braunstein, M. et al., "Transcriptional silencing in yeast is associated with reduced nucleosome acetylation," *Genes Dev.* 7:592-604 (1993).

Burgess, W. et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 111(5 Pt 1):2129-38 (1990).

Chiu, C. & Harley, C., "Replicative senescence and cell immortality: the role of telomeres and telomerase," *Proc. Soc. Exp. Biol. Med.* 214:99-106 (1997).

Chong, L. et al., "A human telomeric protein," *Science* 270:1663-7 (Dec. 1995).

Colman, P., "Effects of amino acid sequence changes on antibody-antigen interactions," *Res. Immunol.* 145(1):33-6 (1994).

Cote, R. et al., "Generation of human monoclonal antibodies reactive with cellular antigens," *Proc. Natl. Acad. Sci. USA* 80:2026-30 (1983).

Counter, C. et al, "Telomere shortening associated with chromosome instability is arrested in immortal cells which express telomerase activity," *EMBO J.* 11(5):1921-9 (1992).

Counter, C. et al., "The catalytic subunit of yeast telomerase," *Proc. Natl. Acad. Sci. USA* 94:9202-7 (Aug. 1997).

Dagarag, M. et al., "Differential impairment of lytic and cytokine functions in senescent human immunodeficiency virus type 1 specific T lymphocytes," *J. Virol.* 77(5):3077-83 (2003).

de Lange, T. et al., "Structure and variability of human chromosome ends," *Mol. Cell. Biol.* 10(2):518-27 (Feb. 1990).

EMBL Database entry Greenberg et al., AF051911, XP002091313 (Apr. 6, 1998).

EMBL Database entry Martin-Rivera et al., AF073311, XP002091314 (Sep. 9, 1998).

Feng, J. et al., "The RNA component of human telomerase," *Science* 269:1236-41 (1995).

Flower, D. "Towards in silico prediction of immunogenic epitopes," *Trends Immunol.* 24(12):667-74 (2003).

Franco, S. et al., "Clonal variation in phenotype and life span of human embryonic fibroblasts (MRC-5) transduced with the catalytic component of telomerase (hTERT)," *Exp. Cell Res.* 268:14-25 (2001).

Freshney, R., *Culture of Animal Cells, A Manual of Basic Technique*, Wiley-Liss, New York, pp. 3-4 (1983).

Frolkis, M. et al., "Dendritic cells reconstituted with human telomerase gene induce potent cytotoxic T-cell response against different types of tumors," *Cancer Gene Ther.* 10:239-49 (2003).

Gearhart, J., "New potential for human embryonic stem cells" *Science* 282:1061-2 (Nov. 6, 1998).

Gray, J. et al., "Cloning and expression of genes for the Oxytricha telomere-binding protein specific subunit interactions in the telomeric complex," *Cell* 67:807-14 (1991).

Greenberg, R. et al., "Expression of mouse telomerase reverse transcriptase during development, differentiation, and proliferation," *Oncogene* 16:1723-30 (1998).

Greener, M., "Telomerase: The search for a universal cancer vaccine," *Mol. Med. Today* 6:257 (2000).

Greenspan, N. & Di Cera, E., "Defining epitopes: It's not as easy as it seems," *Nature Biotech.* 7:936-9 (1999).

Greider, C. & Blackburn, E., "A telomeric sequence in the RNA of Tetrahymena telomerase required for telomere repeat synthesis," *Nature* 337:331-7 (Jan. 1989).

Greider, C., "Telomerase is processive," *Mol. Cell. Biol.* 11:4572-80 (Sep. 1991).

Greider, C., "Telomeres, telomerase and senescence," *BioEssays* 12(8):363-9 (1990).

Greider, C., "Telomerase and senescence: The history, experiment, the future," *Curr. Biol.* 8(5):R178-81 (1998).

Gura, T., "Antisense has growing pains," *Science* 270:575-7 (1995).

Harley, C. & Villeponteau, B., "Telomeres and telomerase in aging and cancer" *Curr. Op. Genet. Dev.* 5:249-255 (1995).

Harley, C. et al., "Telomeres shorten during ageing of human fibroblasts," *Nature* 345:458-60 (1990).

Harley, C., "Telomerase is not an oncogene," *Oncogene* 21:494-502 (2002).

Harley, C., "Telomere loss: Mitotic clock or genetic time bomb?" *Mutation Res.* 256:271-82 (1991).

Harlow, E. & Lane, D., *Antibodies, A Laboratory Manual*, Cold Spring Harbor Laboratory Press, pp. 93-94, 142, 238 (1988).

Harrington, L. et al., "A mammalian telomerase-associated protein," *Science* 275:973-7 (1997).

Harrington, L. et al., "Gel shift and UV cross-linking analysis of Tetrahymena telomerase," *J. Biol. Chem.* 270(15):8893-901 (1995).

Hartman, S. & Mulligan, R., "Two dominant-acting selectable markers for gene transfer studies in mammalian cells," *Proc. Natl. Acad. Sci. USA* 85(21):8047-51 (1988).

Hastie, N. et al., "Telomere eduction in human colorectal carcinoma and with ageing," *Nature* 346:866-8 (1990).

(56) References Cited

OTHER PUBLICATIONS

Haupt, K. et al., "The potential of DNA vaccination against tumor-associated antigens for antitumor therapy," *Exp. Biol. Med.* 227(4):227-37 (2002).

He, T. et al., "A simplified system for generating recombinant adenoviruses," *Proc. Natl. Acad. Sci. USA* 95:2509-14 (1998).

Heiser, A. et al., "Human dendritic cells transfected with renal tumor RNA stimulate polyclonal T-cell responses against antigens expressed by primary and metastatic tumors," *Cancer Res.* 61:3388-93 (2001).

Heiser, A. et al., "Induction of polyclonal prostate cancer-specific CTL using dendritic cells transfected with amplified tumor RNA," *J. Immunol.* 166:2953-60 2001).

Herbert, J. et al., *The Dictionary of Immunology*, 3rd Edition, Academic Press, London, pp. 58-59 (1985).

Herbert, J. et al., *The Dictionary Immunology*, 4th Edition, Academic Press, London. p. 58 (1995).

Hernández, J. et al., "Identification of a human telomerase reverse transcriptase peptide of low affinity for HLA A2.1 that induces cytotoxic T lymphocytes and mediates lysis of tumor cells," *Proc. Natl. Acad. Sci. USA* 99(19):12275-80 (2002).

Hirashima, M. "Ecalectin/galectin-9, a novel eosinophil chemoattractant: Its unction and production," *Int. Arch. Allergy Immunol.* 122(Suppl. 1):6-9 (2000).

Holmes, E., "PSMA specific antibodies and their diagnostic and therapeutic use," *Exp. Opin. Invest. Drugs* 10(3):511-9 (2001).

Huston, J. et al., "Protein engineering of antibody binding sites: Recovery of specific activity in an anti-digoxin single-chain Fv analogue produced in *Escherichia coli*," *Proc. Natl. Acad. Sci. USA* 85:5879-83 (1988).

Ishikawa, F. & Nakayama, J., "A mammalian telomerase component gene TLP1," *Protein Nucleic Acid and Enzyme* 42(9):1407-19 (Jul. 1997). Japanese Language document.

Jiang. D. et al., "Smooth muscle tissues express a major dominant negative splice variant of the type 3 Ca2+ release channel (ryanodine receptor)," *J. Biol. Chem.* 278(7):4763-9 (2003).

Jiang, X-R. et al., "Telomerase expression in human somatic cells does not include changes associated with a transformed phenotype," *Nat. Genet.* 21:111-4 (1999).

Johnstone, A. & Thorpe, R., *Immunochemistry in Practice*, 2nd Ed., Blackwell Scientific Publications, Oxford, pp. 30, 49-50 (1987).

Kim, N. et al., "Specific association of human telomerase activity with immortal cells and cancer," *Science* 266:2011-4 (1994).

Kiyono, T. et al., "Both Rb/p16$^{INK4a}$ inactivation and telomerase activity are required immortalize human epithelial cells," *Nature* 396:84-8 (Nov. 1998).

Klingelhutz, A. et al., "Restoration of telomeres in human papillomavirus-immortalized human anogenital epithelial cells," *Mol. Cell. Biol.* 14(2):961-9 (1994).

Krams, M. et al., "Regulation of telomerase activity by alternate splicing of human telomerase reverse transcriptase mRNA in a subset of neuroblastomas," *Am. J. Pathol.* 159(5):1925-32 (2001).

Lanfranchi, G. et al., "Identification of 4370 epxressed sequence tags from a 3'-end-specific cDNA library of human skeletal muscle by DNA sequencing and filter hybridization," *Genome Res.* 6:35-42 (1996).

Langford, L. et al., "Telomerase activity in ordinary meningiomas predicts poor outcome," *Hum. Pathol.* 28(4):416-20 (1997).

Lazar, E. et al., "Transforming growth factor alpha: mutation of aspartic acid 47 and leucine 48 results in different biological activities," *Mol. Cell. Biol.* 8:1247-52 (1988).

Leem, S. et al., "The human telomerase gene: complete genomic sequence and analysis of tandem repeat polymorphisms in intronic regions," *Oncogene* 21:769-77 (2002).

Lendvay, T. et al., "Senescence mutants of *Saccharomyces cerevisiae* with a defect in telomere replication identify three additional EST genes," *Genetics* 144:1399-412 (Dec. 1996).

Li, H. et al., "Protein phosphatase 2A inhibits nuclear telomerase activity in human breast cancer cells," *J. Biol. Chem.* 272:16729-32 (1997).

Malicki, J. et al., "A human *HOX4B* regulatory element provides head-specific expression in *Drosophila* embryos," *Nature* 358:345-57 (Jul. 23, 1992).

Martin-Rivera, L. et al., "Expression of mouse telomerase catalytic subunit in embryos and adult tissues," *Proc. Natl. Acad. Sci. USA* 95:10471-6 (Sep. 1998).

Meyers, R., Ed., *Molecular Biology and Biotechnology, a Comprehensive Desk Reference*, Wiley-VCH, New York, p. 187 (1995).

Minev, B. et al., "Cytotoxic T cell immunity against telomerase reverse transcriptase in humans," *Proc. Natl. Acad. Sci. USA* 97(9):4796-801 (2000).

Murasawa, S. et al., "Constitutive human telomerase reverse transcriptase expression enhances regenerative properties of endothelial progenitor cells," *Circulation* 106:1133-9 (2002).

Nair, D. et al., "Crystal structure of an antibody bound to an immunodominant peptide epitope: Novel features in peptide-antibody recognition," *J. Immunol.* 165(12):6949-55 (2000).

Nair, S. et al., "Antigen-presenting cells pulsed with unfractionated tumor-derived peptides are potent tumor vaccines," *Eur. J. Immunol.* 27:589-97 (1997).

Nair, S. et al., "Induction of cytotoxic T cell responses and tumor immunity against unrelated tumors using telomerase reverse transcriptase RNA transfected dendritic cells," *Nature Med.* 6(8):1011-7 (2000).

Natarajan, K. et al., "Major histocompatibility complex determinants select T-cell receptor alpha chain variable region dominance in a peptide-specific response," *Proc. Natl. Aced. Sci. USA* 89:8874-8 (Oct. 1992).

Ngo, J. et al., *The Protein Folding Problem and Tertiary Structure Predictor*, Mertz et al., Eds., pp. 433, 492-5 (1994).

O'Hare, M. et al., "Conditional immortalization of freshly isolated human mammary fibroblasts and endothelial cells," *Proc. Natl. Acad. Sci.* 98(2):646-51 (2001).

Ohyashiki, J. et al., "Quantitative relationship between functionally active telomerase and major telomerase components (hTERT and hTR) in acute leukaemia cells," *Brit. J. Cancer* 92:1942-7 (2005).

Parker, K. et al., "Scheme for ranking potential HLA-A2 binding peptides based on independent binding of individual peptide sidechains," *J. Immunol.* 152(1):163-75 (1994).

Pear, W., et al., "Production of high-titer helper-free retroviruses by transient transfection," *Proc. Natl. Acad. Sci USA* 90:8392-6 (1993).

Ping, L. et al., "Dramatic increase of telomerase activity during dendritic cell differentiation and maturation," *J. Leukoc. Biol.* 74:270-6 (2003).

Ramirez, R. et al., "Putative telomere-independent mechanisms of replicative aging reflect inadequate growth conditions," *Genes Dev.* 15:398-403 (2001).

Roitt, I. et al., *Immunology*, 3rd Edition, Mosby, London, pp. 6.4-6.5 (1993).

Roitt, I. et al., *Immunology*, 4th Edition, Mosby, London, pp. 7.7-7.8 (1996).

Rudolph, K. et al., "Inhibition of experimental liver cirrhosis in mice by telomerase gene delivery," *Science* 287:1253-8 (2000).

Sadelain, M. et al., "Generation of high-titer retroviral vector capable of expressing high levels of the human β-globulin gene," *Proc. Natl. Acad. Sci. USA* 92:6728-32 (1995).

Schena, M. et al., "Parallel human genome analysis: Microarray-based expression monitoring of 1000 genes," *Proc. Natl. Acad. Sci. USA* 93:10614-9 (Oct. 1996).

Skolnick, J. & Fetrow, J., "From genes to protein structure and function: Nove applications of computational approaches in the genomic area," *Tibtech* 18:34-9 (2000).

Starling, J. et al., "Extensive telomere repeat arrays in mouse are hypervariable," *Nucl. Acids Res.* 18(23):6881-8 (1990).

Stratagene Catalog, p. 39 (1988).

Su, Z. et al., "Immunological and clinical response in metastatic renal cancer patients vaccinated with tumor RNA-transfected dendritic cells," *Cancer Res.* 63:2127-33 (2003).

Tanaka, T. et al., "Efficient generation of antibodies to oncoprote by using synthetic peptide antigens," *Proc. Natl. Acad. Sci. USA* 82:3400-4 (1985).

Tatematsu, K. et al., *Tissue Culture* 23(1):4-11 (Jan. 1997). Japanese language document.

(56) References Cited

OTHER PUBLICATIONS

Thomson, J. et al., "Embryonic stem cell lines derived from human blastocysts," *Science* 282:1145-7 (Nov. 6, 1998).

Tommerup, H. et al., "Unusual chromatin in human telomeres," *Mol. Cell. Biol.* 14(9):5777-85 (1994).

Trask, B., "Fluorescence in situ hybridization: application in cytogenetics and gene mapping," *Trends Genet.* 7(5):149-54 (1991).

Vaziri, H. & Benchimol, S., "Reconstitution of telomerase activity in normal human cells leads to elongation of telomeres and extended replicative life span," *Curr. Biol.* 8(5):279-82 (1998).

Vonderheide, R. et al., "Vaccination of cancer patients against telomerase induces functional antitumor CD8+ T lymphocytes," *Clin. Cancer Res.* 10:828-39 (2004).

Yi, X. et al., "Quantitation of telomerase components and hTERT mRNA splicing patterns in immortal human cells," *Nucl. Acids Res.* 23:4818-25 (2001).

Yu et al., "In vivo alteration of telomere sequences and senescence caused by mutated Tetrahymena telomerase RNAs," *Nature 344*:126-32 (1990).

Artandi, S. et al., "Telomeres and telomerase in cancer", *Carcinogenesis 31*(1) (2010), pp. 9-18.

Greider, C. et al., "Telomeres, telomerase and cancer", *Sci. Am.* 274(2) (1996), pp. 92-97.

Liu, Y-G. et al., "Thermal asymmetric interlaced PCR: Automatable amplification and sequencing of insert end frqagments from P1 and YAC clones for chromosome walking", *Genomics 25* (1995), pp. 674-681.

Mumby, et al., "Unique properties of monoclonal antibodies as probes of the structure, function and regulation of protein kinasas", *Protein Phosohorylation Book A, Cold Spring Harbor Confernce on Cell Proliferation 8* (1981), pp. 105-124.

\* cited by examiner

```
MPRAPRCRAVRSLLRSHYREVLPLATFVRRLGPQGWRLVQRGDP
AAFRALVAQCLVCVPWDARPPPAAPSFRQVSCLKELVARVLQRL
CERGAKNVLAFGFALLDGARGGPPEAFTTSVRSYLPNTVTDALR
GSGAWGLLLRRVGDDVLVHLLARCALFVLVAPSCAYQVCGPPLY
QLGAATQARPPPHASGPRRRLGCERAWNHSVREAGVPLGLPAPG
ARRRGGSASRSLPLPKRPRRGAAPEPERTPVGQGSWAHPGRTRG
PSDRGFCVVSPARPAEEATSLEGALSGTRHSHPSVGRQHHAGPP
STSRPPRPWDTPCPPVYAETKHFLYSSGDKEQLRPSFLLSSLRP
SLTGARRLVETIFLGSRPWMPGTPRRLPRLPQRYWQMRPLFLEL
LGNHAQCPYGVLLKTHCPLRAAVTPAAGVCAREKPQGSVAAPEE
EDTDPRRLVQLLRQHSSPWQVYGFVRACLRRLVPPGLWGSRHNE
RRFLRNTKKFISLGKHAKLSLQELTWKMSVRDCAWLRRSPGVGC
VPAAEHRLREEILAKFLHWLMSVYVVELLRSFFYVTETTFQKNR
LFFYRKSVWSKLQSIGIRQHLKRVQLRELSEAEVRQHREARPAL
LTSRLRFIPKPDGLRPIVNMDYVVGARTFRREKRAERLTSRVKA
LFSVLNYERARRPGLLGASVLGLDDIHRAWRTFVLRVRAQDPPP
ELYFVKVDVTGAYDTIPQDRLTEVIASIIKPQNTYCVRRYAVVQ
KAAHGHVRKAFKSHVSTLTDLQPYMRQFVAHLQETSPLRDAVVI
EQSSSLNEASSGLFDVFLRFMCHHAVRIRGKSYVQCQGIPQGSI
LSTLLCSLCYGDMENKLFAGIRRDGLLLRLVDDFLLVTPHLTHA
KTFLRTLVRGVPEYGCVVNLRKTVVNFPVEDEALGGTAFVQMPA
HGLFPWCGLLLDTRTLEVQSDYSSYARTSIRASLTFNRGFKAGR
NMRRKLFGVLRLKCHSLFLDLQVNSLQTVCTNIYKILLLQAYRF
HACVLQLPFHQQVWKNPTFFLRVISDTASLCYSILKAKNAGMSL
GAKGAAGPLPSEAVQWLCHQAFLLKLTRHRVTYVPLLGSLRTAQ
TQLSRKLPGTTLTALEAAANPALPSDFKTILD
```

FIG. 1

```
   1 gcagcgctgc gtcctgctgc gcacgtggga agccctggcc ccggccaccc ccgcgatgcc
  61 gcgcgctccc cgctgccgag ccgtgcgctc cctgctgcgc agccactacc gcgaggtgct
 121 gccgctggcc acgttcgtgc ggcgcctggg gccccagggc tggcggctgg tgcagcgcgg
 181 ggacccggcg gctttccgcg cgctggtggc ccagtgcctg tgtgcgtgc cctgggacgc
 241 acggccgccc cccgccgccc cctccttccg ccaggtgtcc tgcctgaagg agctggtggc
 301 ccgagtgctg cagaggctgt gcgagcgcgg cgcgaagaac gtgctggcct tcggcttcgc
 361 gctgctggac ggggcccgcg ggggcccccc cgaggccttc accaccagcg tgcgcagcta
 421 cctgcccaac acggtgaccg acgcactgcg ggggagcggg gcgtggggc tgctgctgcg
 481 ccgcgtgggc gacgacgtgc tggttcacct gctggcacgc tgcgcgctct ttgtgctggt
 541 ggctcccagc tgcgcctacc aggtgtgcgg gccgccgctg taccagctcg gcgctgccac
 601 tcaggcccgg cccccgccac acgctagtgg accccgaagg cgtctgggat gcgaacgggc
 661 ctggaaccat agcgtcaggg aggccggggt ccccctgggc ctgccagccc cgggtgcgag
 721 gaggcgcggg ggcagtgcca gccgaagtct gccgttgccc aagagggccca ggcgtggcgc
 781 tgcccctgag ccggagcgga cgcccgttgg gcagggtccc tgggcccacc cgggcaggac
 841 gcgtggaccg agtgaccgtg gtttctgtgt ggtgtcacct gccagacccg ccgaagaagc
 901 cacctctttg gagggtgcgc tctctggcac gcgccactcc cacccatccg tgggccgcca
 961 gcaccacgcg ggcccccat ccacatcgcg gccaccacgt ccctgggaca cgccttgtcc
1021 cccggtgtac gccgagacca agcacttcct ctactcctca ggcgacaagg agcagctgcg
1081 gccctccttc ctactcagct ctctgaggcc cagcctgact ggcgctcgga ggctcgtgga
1141 gaccatcttt ctgggttcca ggccctggat gccagggact ccccgcaggt tgccccgcct
1201 gccccagcgc tactggcaaa tgcggcccct gtttctggag ctgcttggga accacgcgca
1261 gtgccctac ggggtgctcc tcaagacgca ctgcccgctg cgagctgcgg tcaccccagc
1321 agccggtgtc tgtgcccggg agaagcccca gggctctgtg gcggccccg aggaggagga
1381 cacagacccc cgtcgcctgg tgcagctgct ccgccagcac agcagcccct ggcaggtgta
1441 cggcttcgtg cgggcctgcc tgcgccggct ggtgccccca ggcctctggg gctccaggca
1501 caacgaacgc cgcttcctca ggaacaccca gaagttcatc tccctgggga agcatgccaa
1561 gctctcgctg caggagctga cgtggaagat gagcgtgcgg gactcgcgtt ggctgcgcag
1621 gagcccaggg gttggctgtg ttccggccgc agagcaccgt ctgcgtgagg agatcctggc
1681 caagttcctg cactgctga tgagtgtgta cgtcgtcgag ctgctcaggt ctttctttta
1741 tgtcacggag accacgtttc aaaagaacag gctctttttc taccggaaga gtgtctggag
1801 caagttgcaa agcattggaa tcagacagca cttgaagagg gtgcagctgc gggagctgtc
1861 ggaagcagag gtcaggcagg atcgggaagc caggcccgcc ctgctgacgt ccagactccg
1921 cttcatcccc aagcctgacg ggctgcggcc gattgtgaac atggactacg tcgtgggagc
1981 cagaacgttc cgcagagaaa agagggccga gcgtctcacc tcgagggtga aggcactgtt
2041 cagcgtgctc aactacgagc gggcgcggcg ccccggcctc ctggcgcct ctgtgctggg
2101 cctggacgat atccacaggg cctggcgcac cttcgtgctg cgtgtgcggg cccaggaccc
2161 gccgcctgag ctgtactttg tcaaggtgga tgtgacgggc gcgtacgaca ccatccccca
2221 ggacaggtca acggaggtca tcgccagcat catcaaaccc cagaacacgt actgcgtgcg
2281 tcggtatgcc gtggtccaga aggccgccca tgggcacgtc cgcaaggcct tcaagagcca
2341 cgtctctacc ttgacagacc tccagccgta catgcgacag ttcgtggctc acctgcagga
2401 gaccagcccg ctgagggatg ccgtcgtcat cgagcagagc tcctccctga tgaggccag
2461 cagtggcctc ttcgacgtct tcctacgctt catgtgccac cacgccgtgc gcatcagggg
2521 caagtcctac gtccagtgcc aggggatccc gcagggctcc atcctctcca cgctgctctg
2581 cagcctgtgc tacggcgaca tggagaacaa gctgtttgcg gggattcggg gggacgggct
2641 gctcctgcgt ttggtggatg atttcttgtt ggtgacacct cacctcaccc acgcgaaaac
2701 cttcctcagg accctggtcc gaggtgtccc tgagtatggc tgcgtggtga acttgcggaa
2761 gacagtggtg aacttccctg tagaagacga ggccctgggt ggcacggctt tgttcagat
2821 gccggccac ggcctattcc cctggtgcgg cctgctgctg gatacccgga ccctggaggt
2881 gcagagcgac tactccagct atgcccggac ctccatcaga gccagtctca ccttcaaccg
2941 cggcttcaag gctgggagga acatgcgtcg caaactcttt ggggtcttgc ggctgaagtg
3001 tcacagcctg tttctggatt tgcaggtgaa cagcctccag acggtgtgca ccaacatcta
3061 caagatcctc ctgctgcagg cgtacaggtt tcacgcatgt gtgctgcagc tcccatttca
3121 tcagcaagtt tggaagaacc cacatttttt cctgcgcgtc atctctgaca cggcctccct
3181 ctgctactcc atcctgaaag ccaagaacgc agggatgtcg ctggggcca agggcgccgc
3241 cggccctctg ccctccgagg ccgtgcagtg gctgtgccac caagcattcc tgctcaagct
3301 gactcgacac cgtgtcacct acgtgccact cctggggtca ctcaggacag cccagacgca
3361 gctgagtcgg aagctcccgg ggacgaggct gactgccctg gaggccgcag ccaaccccgc
3421 actgccctca gacttcaaga ccatcctgga ctgatgccaa cccgcccaca ccaggccga
3481 gagcagacac cagcagccct gtcacgccgg gctctacgtc ccaggagggg aggggcggcc
3541 cacacccagg cccgcaccgc tgggagtctg aggcctgagt gagtgtttgg ccgaggcctg
3601 catgtccggc tgaaggctga gtgtccggct gaggcctgag cgagtgtcca gccaagggct
3661 gagtgtccag cacacctgcc gtcttcactt ccccacaggc tggcgctcgg ctccacccca
3721 gggccagctt ttcctcacca ggagccctgc ttccactccc cacataggaa tagtccatcc
3781 ccagattcgc cattgttcac ccctcgccct gccctccttt gccttccacc cccaccatcc
3841 aggtggagac cctgagaagg accctgggag ctctgggaat ttggagtgac caaaggtgtg
3901 ccctgtacac aggcgaggac cctgcacctg gatggggtc cctgtgggtc aaattggggg
3961 gaggtgctgt gggagtaaaa tactgaatat atgagttttt cagttttgaa aaaaa
```

FIG. 2

SEQUENCE LISTING

<160> NUMBER OF SEQ ID NOS: 21

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION: human telomerase reverse transcriptase (hTRT) cDNA

<400> SEQUENCE: 1

```
gcagcgctgc gtcctgctgc gcacgtggga agccctggcc ccggccaccc ccgcg atg        58
                                                              Met
                                                                1 ccg cgc gct ccc cgc tgc cga gcc gtg cgc tcc ctg ctg cgc agc cac        106
Pro Arg Ala Pro Arg Cys Arg Ala Val Arg Ser Leu Leu Arg Ser His
             5                  10                  15 tac cgc gag gtg ctg ccg ctg gcc acg ttc gtg cgg cgc ctg ggg ccc        154
Tyr Arg Glu Val Leu Pro Leu Ala Thr Phe Val Arg Arg Leu Gly Pro
         20                  25                  30 cag ggc tgg cgg ctg gtg cag cgc ggg gac ccg gcg gct ttc cgc gcg        202
Gln Gly Trp Arg Leu Val Gln Arg Gly Asp Pro Ala Ala Phe Arg Ala
     35                  40                  45 ctg gtg gcc cag tgc ctg gtg tgc gtg ccc tgg gac gca cgg ccg ccc        250
Leu Val Ala Gln Cys Leu Val Cys Val Pro Trp Asp Ala Arg Pro Pro
 50                  55                  60                  65 ccc gcc gcc ccc tcc ttc cgc cag gtg tcc tgc ctg aag gag ctg gtg        298
Pro Ala Ala Pro Ser Phe Arg Gln Val Ser Cys Leu Lys Glu Leu Val
                 70                  75                  80 gcc cga gtg ctg cag agg ctg tgc gag cgc ggc gcg aag aac gtg ctg        346
Ala Arg Val Leu Gln Arg Leu Cys Glu Arg Gly Ala Lys Asn Val Leu
             85                  90                  95 gcc ttc ggc ttc gcg ctg ctg gac ggg gcc cgg ggg ggc ccc ccc gag        394
Ala Phe Gly Phe Ala Leu Leu Asp Gly Ala Arg Gly Gly Pro Pro Glu
         100                 105                 110 gcc ttc acc acc agc gtg cgc agc tac ctg ccc aac acg gtg acc gac        442
Ala Phe Thr Thr Ser Val Arg Ser Tyr Leu Pro Asn Thr Val Thr Asp
     115                 120                 125 gca ctg cgg ggg agc ggg gcg tgg ggg ctg ctg ctg cgc cgc gtg ggc        490
Ala Leu Arg Gly Ser Gly Ala Trp Gly Leu Leu Leu Arg Arg Val Gly
130                 135                 140                 145 gac gac gtg ctg gtt cac ctg ctg gca cgc tgc gcg ctc ttt gtg ctg        538
Asp Asp Val Leu Val His Leu Leu Ala Arg Cys Ala Leu Phe Val Leu
                 150                 155                 160 gtg gct ccc agc tgc gcc tac cag gtg tgc ggg ccg ccg ctg tac cag        586
Val Ala Pro Ser Cys Ala Tyr Gln Val Cys Gly Pro Pro Leu Tyr Gln
             165                 170                 175 ctc ggc gct gcc act cag gcc cgg ccc ccg cca cac gct agt gga ccc        634
Leu Gly Ala Ala Thr Gln Ala Arg Pro Pro Pro His Ala Ser Gly Pro
         180                 185                 190 cga agg cgt ctg gga tgc gaa cgg gcc tgg aac cat agc gtc agg gag        682
Arg Arg Arg Leu Gly Cys Glu Arg Ala Trp Asn His Ser Val Arg Glu
     195                 200                 205 gcc ggg gtc ccc ctg ggc ctg cca gcc ccg ggt gcg agg agg cgc ggg        730
Ala Gly Val Pro Leu Gly Leu Pro Ala Pro Gly Ala Arg Arg Arg Gly
210                 215                 220                 225 ggc agt gcc agc cga agt ctg ccg ttg ccc aag agg ccc agg cgt ggc        778
Gly Ser Ala Ser Arg Ser Leu Pro Leu Pro Lys Arg Pro Arg Arg Gly
                 230                 235                 240
```

```
gct gcc cct gag ccg gag cgg acg ccc gtt ggg cag ggg tcc tgg gcc        826
Ala Ala Pro Glu Pro Glu Arg Thr Pro Val Gly Gln Gly Ser Trp Ala
            245                 250                 255 cac ccg ggc agg acg cgt gga ccg agt gac cgt ggt ttc tgt gtg gtg        874
His Pro Gly Arg Thr Arg Gly Pro Ser Asp Arg Gly Phe Cys Val Val
            260                 265                 270 tca cct gcc aga ccc gcc gaa gaa gcc acc tct ttg gag ggt gcg ctc        922
Ser Pro Ala Arg Pro Ala Glu Glu Ala Thr Ser Leu Glu Gly Ala Leu
        275                 280                 285 tct ggc acg cgc cac tcc cac cca tcc gtg ggc cgc cag cac cac gcg        970
Ser Gly Thr Arg His Ser His Pro Ser Val Gly Arg Gln His His Ala
290                 295                 300                 305 ggc ccc cca tcc aca tcg cgg cca cca cgt ccc tgg gac acg cct tgt       1018
Gly Pro Pro Ser Thr Ser Arg Pro Pro Arg Pro Trp Asp Thr Pro Cys
                310                 315                 320 ccc ccg gtg tac gcc gag acc aag cac ttc ctc tac tcc tca ggc gac       1066
Pro Pro Val Tyr Ala Glu Thr Lys His Phe Leu Tyr Ser Ser Gly Asp
            325                 330                 335 aag gag cag ctg cgg ccc tcc ttc cta ctc agc tct ctg agg ccc agc       1114
Lys Glu Gln Leu Arg Pro Ser Phe Leu Leu Ser Ser Leu Arg Pro Ser
        340                 345                 350 ctg act ggc gct cgg agg ctc gtg gag acc atc ttt ctg ggt tcc agg       1162
Leu Thr Gly Ala Arg Arg Leu Val Glu Thr Ile Phe Leu Gly Ser Arg
    355                 360                 365 ccc tgg atg cca ggg act ccc cgc agg ttg ccc cgc ctg ccc cag cgc       1210
Pro Trp Met Pro Gly Thr Pro Arg Arg Leu Pro Arg Leu Pro Gln Arg
370                 375                 380                 385 tac tgg caa atg cgg ccc ctg ttt ctg gag ctg ctt ggg aac cac gcg       1258
Tyr Trp Gln Met Arg Pro Leu Phe Leu Glu Leu Leu Gly Asn His Ala
                390                 395                 400 cag tgc ccc tac ggg gtg ctc ctc aag acg cac tgc ccg ctg cga gct       1306
Gln Cys Pro Tyr Gly Val Leu Leu Lys Thr His Cys Pro Leu Arg Ala
            405                 410                 415 gcg gtc acc cca gca gcc ggt gtc tgt gcc cgg gag aag ccc cag ggc       1354
Ala Val Thr Pro Ala Ala Gly Val Cys Ala Arg Glu Lys Pro Gln Gly
        420                 425                 430 tct gtg gcg gcc ccc gag gag gag gac aca gac ccc gtc gcc tg gtg       1402
Ser Val Ala Ala Pro Glu Glu Glu Asp Thr Asp Pro Arg Arg Leu Val
    435                 440                 445 cag ctg ctc cgc cag cac agc agc ccc tgg cag gtg tac ggc ttc gtg       1450
Gln Leu Leu Arg Gln His Ser Ser Pro Trp Gln Val Tyr Gly Phe Val
450                 455                 460                 465 cgg gcc tgc ctg cgc cgg ctg gtg ccc cca ggc ctc tgg ggc tcc agg       1498
Arg Ala Cys Leu Arg Arg Leu Val Pro Pro Gly Leu Trp Gly Ser Arg
                470                 475                 480 cac aac gaa cgc cgc ttc ctc agg aac acc aag aag ttc atc tcc ctg       1546
His Asn Glu Arg Arg Phe Leu Arg Asn Thr Lys Lys Phe Ile Ser Leu
            485                 490                 495 ggg aag cat gcc aag ctc tcg ctg cag gag ctg acg tgg aag atg agc       1594
Gly Lys His Ala Lys Leu Ser Leu Gln Glu Leu Thr Trp Lys Met Ser
        500                 505                 510 gtg cgg gac tgc gct tgg ctg cgc agg agc cca ggg gtt ggc tgt gtt       1642
Val Arg Asp Cys Ala Trp Leu Arg Arg Ser Pro Gly Val Gly Cys Val
    515                 520                 525 ccg gcc gca gag cac cgt ctg cgt gag gag atc ctg gcc aag ttc ctg       1690
Pro Ala Ala Glu His Arg Leu Arg Glu Glu Ile Leu Ala Lys Phe Leu
530                 535                 540                 545 cac tgg ctg atg agt gtg tac gtc gtc gag ctg ctc agg tct ttc ttt       1738
His Trp Leu Met Ser Val Tyr Val Val Glu Leu Leu Arg Ser Phe Phe
                550                 555                 560
```

```
tat gtc acg gag acc acg ttt caa aag aac agg ctc ttt ttc tac cgg      1786
Tyr Val Thr Glu Thr Thr Phe Gln Lys Asn Arg Leu Phe Phe Tyr Arg
            565                 570                 575 aag agt gtc tgg agc aag ttg caa agc att gga atc aga cag cac ttg      1834
Lys Ser Val Trp Ser Lys Leu Gln Ser Ile Gly Ile Arg Gln His Leu
            580                 585                 590 aag agg gtg cag ctg cgg gag ctg tcg gaa gca gag gtc agg cag cat      1882
Lys Arg Val Gln Leu Arg Glu Leu Ser Glu Ala Glu Val Arg Gln His
    595                 600                 605 cgg gaa gcc agg ccc gcc ctg ctg acg tcc aga ctc cgc ttc atc ccc      1930
Arg Glu Ala Arg Pro Ala Leu Leu Thr Ser Arg Leu Arg Phe Ile Pro
610                 615                 620                 625 aag cct gac ggg ctg cgg ccg att gtg aac atg gac tac gtc gtg gga      1978
Lys Pro Asp Gly Leu Arg Pro Ile Val Asn Met Asp Tyr Val Val Gly
            630                 635                 640 gcc aga acg ttc cgc aga gaa aag agg gcc gag cgt ctc acc tcg agg      2026
Ala Arg Thr Phe Arg Arg Glu Lys Arg Ala Glu Arg Leu Thr Ser Arg
            645                 650                 655 gtg aag gca ctg ttc agc gtg ctc aac tac gag cgg gcg cgg cgc ccc      2074
Val Lys Ala Leu Phe Ser Val Leu Asn Tyr Glu Arg Ala Arg Arg Pro
            660                 665                 670 ggc ctc ctg ggc gcc tct gtg ctg ggc ctg gac gat atc cac agg gcc      2122
Gly Leu Leu Gly Ala Ser Val Leu Gly Leu Asp Asp Ile His Arg Ala
    675                 680                 685 tgg cgc acc ttc gtg ctg cgt gtg cgg gcc cag gac ccg ccg cct gag      2170
Trp Arg Thr Phe Val Leu Arg Val Arg Ala Gln Asp Pro Pro Pro Glu
690                 695                 700                 705 ctg tac ttt gtc aag gtg gat gtg acg ggc gcg tac gac acc atc ccc      2218
Leu Tyr Phe Val Lys Val Asp Val Thr Gly Ala Tyr Asp Thr Ile Pro
            710                 715                 720 cag gac agg ctc acg gag gtc atc gcc agc atc atc aaa ccc cag aac      2266
Gln Asp Arg Leu Thr Glu Val Ile Ala Ser Ile Ile Lys Pro Gln Asn
            725                 730                 735 acg tac tgc gtg cgt cgg tat gcc gtg gtc cag aag gcc gcc cat ggg      2314
Thr Tyr Cys Val Arg Arg Tyr Ala Val Val Gln Lys Ala Ala His Gly
            740                 745                 750 cac gtc cgc aag gcc ttc aag agc cac gtc tct acc ttg aca gac ctc      2362
His Val Arg Lys Ala Phe Lys Ser His Val Ser Thr Leu Thr Asp Leu
755                 760                 765 cag ccg tac atg cga cag ttc gtg gct cac ctg cag gag acc agc ccg      2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc      2458
Leu Arg Asp Ala Val Val Ile Glu Gln Ser Ser Ser Leu Asn Glu Ala
            790                 795                 800 agc agt ggc ctc ttc gac gtc ttc cta cgc ttc atg tgc cac cac gcc      2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag      2554
Val Arg Ile Arg Gly Lys Ser Tyr Val Gln Cys Gln Gly Ile Pro Gln
            820                 825                 830 ggc tcc atc ctc tcc acg ctg ctc tgc agc ctg tgc tac ggc gac atg      2602
Gly Ser Ile Leu Ser Thr Leu Leu Cys Ser Leu Cys Tyr Gly Asp Met
    835                 840                 845 gag aac aag ctg ttt gcg ggg att cgg cgg gac ggg ctg ctc ctg cgt      2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa      2698
Leu Val Asp Asp Phe Leu Leu Val Thr Pro His Leu Thr His Ala Lys
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 870 |     |     |     | 875 |     |     |     | 880 |     |     |     |      |
| acc | ttc | ctc | agg | acc | ctg | gtc | cga | ggt | gtc | cct | gag | tat | ggc | tgc | gtg | 2746 |
| Thr | Phe | Leu | Arg | Thr | Leu | Val | Arg | Gly | Val | Pro | Glu | Tyr | Gly | Cys | Val |      |
|     |     |     | 885 |     |     |     |     | 890 |     |     |     |     | 895 |     |     |      |
| gtg | aac | ttg | cgg | aag | aca | gtg | gtg | aac | ttc | cct | gta | gaa | gac | gag | gcc | 2794 |
| Val | Asn | Leu | Arg | Lys | Thr | Val | Val | Asn | Phe | Pro | Val | Glu | Asp | Glu | Ala |      |
|     |     |     | 900 |     |     |     |     | 905 |     |     |     |     | 910 |     |     |      |
| ctg | ggt | ggc | acg | gct | ttt | gtt | cag | atg | ccg | gcc | cac | ggc | cta | ttc | ccc | 2842 |
| Leu | Gly | Gly | Thr | Ala | Phe | Val | Gln | Met | Pro | Ala | His | Gly | Leu | Phe | Pro |      |
|     |     |     | 915 |     |     |     |     | 920 |     |     |     |     | 925 |     |     |      |
| tgg | tgc | ggc | ctg | ctg | ctg | gat | acc | cgg | acc | ctg | gag | gtg | cag | agc | gac | 2890 |
| Trp | Cys | Gly | Leu | Leu | Leu | Asp | Thr | Arg | Thr | Leu | Glu | Val | Gln | Ser | Asp |      |
| 930 |     |     |     |     | 935 |     |     |     |     | 940 |     |     |     |     | 945 |      |
| tac | tcc | agc | tat | gcc | cgg | acc | tcc | atc | aga | gcc | agt | ctc | acc | ttc | aac | 2938 |
| Tyr | Ser | Ser | Tyr | Ala | Arg | Thr | Ser | Ile | Arg | Ala | Ser | Leu | Thr | Phe | Asn |      |
|     |     |     |     | 950 |     |     |     |     | 955 |     |     |     |     | 960 |     |      |
| cgc | ggc | ttc | aag | gct | ggg | agg | aac | atg | cgt | cgc | aaa | ctc | ttt | ggg | gtc | 2986 |
| Arg | Gly | Phe | Lys | Ala | Gly | Arg | Asn | Met | Arg | Arg | Lys | Leu | Phe | Gly | Val |      |
|     |     |     | 965 |     |     |     |     | 970 |     |     |     |     | 975 |     |     |      |
| ttg | cgg | ctg | aag | tgt | cac | agc | ctg | ttt | ctg | gat | ttg | cag | gtg | aac | agc | 3034 |
| Leu | Arg | Leu | Lys | Cys | His | Ser | Leu | Phe | Leu | Asp | Leu | Gln | Val | Asn | Ser |      |
|     |     |     | 980 |     |     |     |     | 985 |     |     |     |     | 990 |     |     |      |
| ctc | cag | acg | gtg | tgc | acc | aac | atc | tac | aag | atc | ctc | ctg | cag | gcg | | 3082 |
| Leu | Gln | Thr | Val | Cys | Thr | Asn | Ile | Tyr | Lys | Ile | Leu | Leu | Gln | Ala |     |      |
|     | 995 |     |     |     |     | 1000|     |     |     |     | 1005|     |     |     |     |      |
| tac | agg | ttt | cac | gca | tgt | gtg | ctg | cag | ctc | cca | ttt | cat | cag | caa | gtt | 3130 |
| Tyr | Arg | Phe | His | Ala | Cys | Val | Leu | Gln | Leu | Pro | Phe | His | Gln | Gln | Val |      |
| 1010|     |     |     |     | 1015|     |     |     |     | 1020|     |     |     |     | 1025|      |
| tgg | aag | aac | ccc | aca | ttt | ttc | ctg | cgc | gtc | atc | tct | gac | acg | gcc | tcc | 3178 |
| Trp | Lys | Asn | Pro | Thr | Phe | Phe | Leu | Arg | Val | Ile | Ser | Asp | Thr | Ala | Ser |      |
|     |     |     |     | 1030|     |     |     |     | 1035|     |     |     |     | 1040|     |      |
| ctc | tgc | tac | tcc | atc | ctg | aaa | gcc | aag | aac | gca | ggg | atg | tcg | ctg | ggg | 3226 |
| Leu | Cys | Tyr | Ser | Ile | Leu | Lys | Ala | Lys | Asn | Ala | Gly | Met | Ser | Leu | Gly |      |
|     |     |     |     | 1045|     |     |     |     | 1050|     |     |     |     | 1055|     |      |
| gcc | aag | ggc | gcc | gcc | ggc | cct | ctg | ccc | tcc | gag | gcc | gtg | cag | tgg | ctg | 3274 |
| Ala | Lys | Gly | Ala | Ala | Gly | Pro | Leu | Pro | Ser | Glu | Ala | Val | Gln | Trp | Leu |      |
|     |     |     | 1060|     |     |     |     | 1065|     |     |     |     | 1070|     |     |      |
| tgc | cac | caa | gca | ttc | ctg | ctc | aag | ctg | act | cga | cac | cgt | gtc | acc | tac | 3322 |
| Cys | His | Gln | Ala | Phe | Leu | Leu | Lys | Leu | Thr | Arg | His | Arg | Val | Thr | Tyr |      |
|     |     | 1075|     |     |     |     | 1080|     |     |     |     | 1085|     |     |     |      |
| gtg | cca | ctc | ctg | ggg | tca | ctc | agg | aca | gcc | cag | acg | cag | ctg | agt | cgg | 3370 |
| Val | Pro | Leu | Leu | Gly | Ser | Leu | Arg | Thr | Ala | Gln | Thr | Gln | Leu | Ser | Arg |      |
| 1090|     |     |     | 1095|     |     |     |     | 1100|     |     |     |     | 1105|     |      |
| aag | ctc | ccg | ggg | acg | acg | ctg | act | gcc | ctg | gag | gcc | gca | gcc | aac | ccg | 3418 |
| Lys | Leu | Pro | Gly | Thr | Thr | Leu | Thr | Ala | Leu | Glu | Ala | Ala | Ala | Asn | Pro |      |
|     |     |     | 1110|     |     |     |     | 1115|     |     |     |     | 1120|     |     |      |
| gca | ctg | ccc | tca | gac | ttc | aag | acc | atc | ctg | gac | tga | tggccacccg |   |   |   | 3464 |
| Ala | Leu | Pro | Ser | Asp | Phe | Lys | Thr | Ile | Leu | Asp |     |     |     |     |     |      |
|     |     |     | 1125|     |     |     |     | 1130|     |     |     |     |     |     |     |      | cccacagcca ggccgagagc agacaccagc agccctgtca cgccgggctc tacgtcccag  3524 ggagggaggg gcggcccaca cccaggcccg caccgctggg agtctgaggc ctgagtgagt  3584 gtttggccga ggcctgcatg tccggctgaa ggctgagtgt ccggctgagg cctgagcgag  3644 tgtccagcca agggctgagt gtccagcaca cctgccgtct tcacttcccc acaggctggc  3704 gctcggctcc accccagggc cagcttttcc tcaccaggag cccggcttcc actcccaca  3764 taggaatagt ccatcccag attgccatt gttcacccct cgccctgccc tcctttgcct  3824 tccaccccca ccatccaggt ggagaccctg agaaggaccc tgggagctct gggaatttgg  3884

```
agtgaccaaa ggtgtgccct gtacacaggc gaggaccctg cacctggatg ggggtccctg    3944
tgggtcaaat tgggggggagg tgctgtggga gtaaaatact gaatatatga gttttttcagt  4004 tttgaaaaaa a                                                          4015
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
```

```
                    340                 345                 350
    Ser Leu Thr Gly Ala Arg Arg Leu Val Glu Thr Ile Phe Leu Gly Ser
                355                 360                 365

Arg Pro Trp Met Pro Gly Thr Pro Arg Arg Leu Pro Arg Leu Pro Gln
                370                 375                 380

Arg Tyr Trp Gln Met Arg Pro Leu Phe Leu Glu Leu Leu Gly Asn His
    385                 390                 395                 400

Ala Gln Cys Pro Tyr Gly Val Leu Leu Lys Thr His Cys Pro Leu Arg
                    405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
                450                 455                 460

Val Arg Ala Cys Leu Arg Arg Leu Val Pro Pro Gly Leu Trp Gly Ser
    465                 470                 475                 480

Arg His Asn Glu Arg Arg Phe Leu Arg Asn Thr Lys Lys Phe Ile Ser
                    485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
                530                 535                 540

Leu His Trp Leu Met Ser Val Tyr Val Val Glu Leu Leu Arg Ser Phe
    545                 550                 555                 560

Phe Tyr Val Thr Glu Thr Thr Phe Gln Lys Asn Arg Leu Phe Phe Tyr
                    565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
    625                 630                 635                 640

Gly Ala Arg Thr Phe Arg Arg Glu Lys Arg Ala Glu Arg Leu Thr Ser
                    645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro Pro
                690                 695                 700

Glu Leu Tyr Phe Val Lys Val Asp Val Thr Gly Ala Tyr Asp Thr Ile
    705                 710                 715                 720

Pro Gln Asp Arg Leu Thr Glu Val Ile Ala Ser Ile Ile Lys Pro Gln
                    725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765
```

```
Leu Gln Pro Tyr Met Arg Gln Phe Val Ala His Leu Gln Glu Thr Ser
            770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
            980                 985                 990
Ser Leu Gln Thr Val Cys Thr Asn Ile Tyr Lys Ile Leu Leu Leu Gln
        995                 1000                1005
Ala Tyr Arg Phe His Ala Cys Val Leu Gln Leu Pro Phe His Gln Gln
1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
                1045                1050                1055
Gly Ala Lys Gly Ala Ala Gly Pro Leu Pro Ser Glu Ala Val Gln Trp
            1060                1065                1070
Leu Cys His Gln Ala Phe Leu Leu Lys Leu Thr Arg His Arg Val Thr
        1075                1080                1085
Tyr Val Pro Leu Leu Gly Ser Leu Arg Thr Ala Gln Thr Gln Leu Ser
1090                1095                1100
Arg Lys Leu Pro Gly Thr Thr Leu Thr Ala Leu Glu Ala Ala Ala Asn
1105                1110                1115                1120
Pro Ala Leu Pro Ser Asp Phe Lys Thr Ile Leu Asp
                1125                1130

<210> SEQ ID NO 3
<211> LENGTH: 6
<212> TYPE: PRT
<213> ORGANISM: Homo sapiens
<220> FEATURE:
<221> NAME/KEY: PEPTIDE
<222> LOCATION: (1)..(6)
<223> OTHER INFORMATION: amino acid positions 560-565 from hTRT
```

-continued

<400> SEQUENCE: 3

Phe Phe Tyr Val Thr Glu
 1               5

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: amino acid positions 405-418 from hTRT

<400> SEQUENCE: 4

Tyr Gly Val Leu Leu Lys Thr His Cys Pro Leu Arg Ala Ala
 1               5                   10

<210> SEQ ID NO 5
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: amino acid positions 561-564 from hTRT

<400> SEQUENCE: 5

Phe Tyr Val Thr
 1

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:RT1 oligo

<400> SEQUENCE: 6
gaaggccgcc cacgggcacg tccgc                                        25

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:RT2 oligo

<400> SEQUENCE: 7
cccggccacc ccagccatgg cgcgcgctcc cc                                32

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:RT5 oligo

<400> SEQUENCE: 8 tacgggtgc tcctcaagac gcactgcccg ctgctccgcc agcacagcag ccctggcag    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:RT10 oligo -continued

<400> SEQUENCE: 9
tactccatcc tgaaagccaa gaacgcaggg ctgtgccacc aagcattcct gctcaagctg     60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:RT11 oligo

<400> SEQUENCE: 10
ctgtgccacc aagcattcct gctcaagctg gccgcagcca cccggcact gccctcagac     60

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence:RT3A oligo

<400> SEQUENCE: 11
actcaggccc ggcccccgcc acacgctagc gagaccaagc acttcctcta ctcctcaggc     60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence:RT4A oligo

<400> SEQUENCE: 12
actcaggccc ggcccccgcc acacgctagc gtggtgtcac ctgccagacc cgccgaagaa     60

<210> SEQ ID NO 13
<211> LENGTH: 69
<212> TYPE: DNA
<213> ORGANISM: Artificial Sequence
<220> FEATURE:
<223> OTHER INFORMATION: Description of Artificial Sequence:RT6A oligo

<400> SEQUENCE: 13
atccccaagc ctgacgggct gcggccgatt gttaacatgc tgttcagcgt gctcaactac     60
gagcgggcg                                                            69

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence:RT8A oligo

<400> SEQUENCE: 14
acgtactgcg tgcgtcggta tgccgtggtc acagatctcc agccgtacat gcgacagttc     60
gtg                                                                  63

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence:RT3A/5 oligo

<400> SEQUENCE: 15
actcaggccc ggcccccgcc acacgctagc ctgctccgcc agcacagcag cccctggcag    60

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence:LM121-WG
      oligo

<400> SEQUENCE: 16
gttcagatgc cggcccacgg cctattccct ctagatacccc ggaccctgga ggtgcagagc    60
gac                                                                  63

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence:LM122-Nuc
      oligo

<400> SEQUENCE: 17
ccctgggcct gccagccccg ggtgccggcg ctgcccctga gccggagcgg              50

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence:RT3 oligo

<400> SEQUENCE: 18
gctagtggac cccgaaggcg tctgggatgc gagaccaagc acttcctcta ctcctcaggc    60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence:RT4 oligo

<400> SEQUENCE: 19
gctagtggac cccgaaggcg tctgggatgc gtggtgtcac ctgccagacc cgccgaagaa    60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:RT6 oligo

<400> SEQUENCE: 20
gacgggctgc ggccgattgt gaacatggac ctgttcagcg tgctcaacta cgagcgggcg    60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence:RT8 oligo

<400> SEQUENCE: 21
acgtactgcg tgcgtcggta tgccgtggtc accttgacag acctccagcc gtacatgcga    60

NUCLEIC ACIDS ENCODING INACTIVE VARIANTS OF HUMAN TELOMERASE

CROSS-REFERENCE TO RELATED APPLICATIONS

This application is a divisional of U.S. patent application Ser. No. 09/990,080, filed Nov. 21, 2001 (now U.S. Pat. No. 7,091,021); which is a continuation of U.S. patent application Ser. No. 09/128,354, filed Aug. 3, 1998 (now U.S. Pat. No. 6,337,200); which is a continuation-in-part of U.S. patent application Ser. No. 09/052,864, filed Mar. 31, 1998 (abandoned).

The aforelisted priority applications are hereby incorporated herein by reference in their entirety, as are the following: U.S. patent application Ser. Nos. 08/851,843; 08/854,050; 08/911,312; 08/912,951; 08/915,503; 08/974,549; and 08/974,584; and International Patent Publications WO 98/14592 and WO 98/14593.

BACKGROUND

The following discussion is intended to introduce the field of the present invention to the reader. The citation of various references in this section should not be construed as an admission of prior invention.

It has long been recognized that complete replication of the ends of eukaryotic chromosomes requires specialized cell components (Watson, 1972, *Nature New Biol.*, 239:197; Olovnikov, 1973, *J. Theor. Biol.*, 41:181). Replication of a linear DNA strand by conventional DNA polymerase requires an RNA primer, and can proceed only 5' to 3'. When the RNA bound at the extreme 5' ends of eukaryotic chromosomal DNA strands is removed, a gap is introduced, leading to a progressive shortening of daughter strands with each round of replication. This shortening of telomeres, the protein-DNA structures physically located on the ends of chromosomes, is thought to account for the phenomenon of cellular senescence or aging of normal human somatic cells in vitro and in vivo. The maintenance of telomeres is a function of a telomere-specific DNA polymerase known as telomerase. Telomerase is a ribonucleoprotein (RNP) that uses a portion of its RNA moiety as a template for telomeric DNA synthesis (Morin, 1997, *Eur. J. Cancer* 33:750). The length and integrity of telomeres and the telomerase expression status of a cell is thus related to entry of a cell into a senescent stage (i.e., loss of proliferative capacity), or the ability of a cell to escape senescence, i.e., to become immortal.

Consistent with the relationship of telomeres and telomerase to the proliferative capacity of a cell (i.e., the ability of the cell to divide indefinitely), telomerase activity is detected in immortal cell lines and an extraordinarily diverse set of tumor tissues, but is not detected (i.e., was absent or below the assay threshold) in normal somatic cell cultures or normal tissues adjacent to a tumor (see, U.S. Pat. Nos. 5,629,154; 5,489,508; 5,648,215; and 5,639,613; see also, Morin, 1989, *Cell* 59: 521; Shay and Bacchetti 1997, *Eur. J. Cancer* 33:787; Kim et al., 1994, *Science* 266:2011; Counter et al., 1992, *EMBO J.* 11:1921; Counter et al., 1994, *Proc. Natl. Acad. Sci. U.S.A.* 91, 2900; Counter et al., 1994, *J. Virol.* 68:3410). Moreover, a correlation between the level of telomerase activity in a tumor and the likely clinical outcome of the patient has been reported (e.g., U.S. Pat. No. 5,639,613, supra; Langford et al., 1997, *Hum. Pathol.* 28:416). Thus, human telomerase is an ideal target for diagnosing and treating human diseases relating to cellular proliferation and senescence, such as cancer, or for increasing the proliferative capacity of a cell.

SUMMARY

In one aspect, the invention provides an isolated or recombinant hTRT polypeptide that has telomerase catalytic activity. In one embodiment, the hTRT polypeptide has a deletion of at least 25 residues in the regions corresponding to residues 192-323, 200-323, 192-271, 200-271, 222-240, 415-450, 192-323 and 415-450, or 192-271 and 415-450 of hTRT. In a related embodiment, residues 192-323, 200-323, 192-271, 200-271, 222-240, 415-450, 192-323 and 415-450, or 192-271 and 415-450 of hTRT are deleted. The invention also provides a polynucleotide comprising a nucleotide sequence encoding these hTRT polypeptides. In some embodiments, the polynucleotide includes a promoter sequence operably linked to the nucleotide sequence encoding the hTRT polypeptide.

The invention also provides a method of preparing recombinant telomerase by contacting a recombinant hTRT polypeptide containing a deletion as described supra with a telomerase RNA component under conditions such that the recombinant protein and the telomerase RNA component associate to form a telomerase enzyme capable of catalyzing the addition of nucleotides to a telomerase substrate. The hTRT polypeptide may be produced in an in vitro expression system and/or may be purified before the contacting step. In some embodiments, the contacting occurs in a cell.

The invention further provides a method for increasing the proliferative capacity of a vertebrate cell by introducing into a cell the recombinant hTRT polynucleotide encoding an hTRT deletion variant described supra. In a related embodiment, the invention provides a cell, such as a human cell or other mammalian cell, comprising a nucleotide sequence that encodes the hTRT deletion variant polypeptide. The invention provides such cells that have an increased proliferative capacity relative to a cell that is otherwise identical but does not comprise the recombinant polynucleotide.

In a different aspect of the invention, an isolated or recombinant hTRT polypeptide that has a deletion of amino acid residues 192-450, 560-565, 637-660, 638-660, 748-766, 748-764, or 1055-1071, where the residue numbering is with reference to the hTRT polypeptide having the sequence provided in FIG. 1, is provided. In one embodiment, the hTRT protein fragment has at least 6 amino acid residues. In other embodiments, the hTRT protein fragment has at least 8, at least about 10, at least about 12, at least about 15, or at least about 20 contiguous amino acid residues of a naturally occurring hTRT polypeptide. In still other embodiments, the hTRT protein fragment has at least about 50 or at least about 100 amino acid residues. In a related aspect, the invention provides an isolated, recombinant, or substantially purified polynucleotide encoding this polypeptide, which in some embodiments includes a promoter sequence operably linked to the nucleotide sequence encoding the hTRT polypeptide.

The invention also provides a method of reducing telomerase activity in a cell by introducing the polynucleotide described supra (i.e., having a deletion of amino acid residues 192-450, 560-565, 637-660, 638-660, 748-766, 748-764, or 1055-1071) into a cell under conditions in which it is expressed.

In a related embodiment, the hTRT polypeptide has one or more mutations other than, or in addition to, a deletion of at least 25 residues in the regions corresponding to residues 192-323, 200-323, 192-271, 200-271, 222-240, 415-450, 192-323 and 415-450, or 192-271 and 415-450 of hTRT.

DRAWINGS

FIG. 1 shows the amino acid sequence of a 1132-residue human telomerase reverse transcriptase (hTRT) protein (SEQ ID NO:2).

FIG. 2 shows the nucleotide sequence of a naturally occurring cDNA encoding the hTRT protein (SEQ ID NO:1).

DETAILED DESCRIPTION

I. Introduction

Telomerase is a ribonucleoprotein complex (RNP) comprising an RNA component and a catalytic protein component. The catalytic protein component of human telomerase, hereinafter referred to as telomerase reverse transcriptase ("hTRT"), has been cloned, and protein, cDNA and genomic sequences determined. See, e.g., Nakamura et al., 1997, Science 277:955, and U.S. Pat. Nos. 6,475,789 and 6,166,178. The sequence of a full-length native hTRT has been deposited in GenBank (Accession No. AF015950), and plasmid and phage vectors having hTRT coding sequences have been deposited with the American Type Culture Collection, Rockville, Md. (accession numbers 209024, 209016, and 98505). The catalytic subunit protein of human telomerase has also been referred to as "hEST2" (Meyerson et al., 1997, Cell 90:785), "hTCS1" (Kilian et al., 1997, Hum. Mol. Genet. 6:2011), "TP2" (Harrington et al., 1997, Genes Dev. 11:3109), and "hTERT" (e.g., Greider, 1998, Curr. Biol 8:R178-R181). Human TRT is also described in the aforereferenced priority applications and U.S. patent application Ser. Nos. 08/846,017, 08/844,419, and 08/724,643. The RNA component of human telomerase (hTR) has also been characterized (see U.S. Pat. No. 5,583,016). All of the aforementioned applications and publications are incorporated by reference herein in their entirety and for all purposes.

Human TRT is of extraordinary interest and value because, inter alia, telomerase activity in human cells and other mammalian cells correlates with cell proliferative capacity, cell immortality, and the development of a neoplastic phenotype. Thus, hTRT polypeptides, including the hTRT variants described herein, and polynucleotides encoding hTRT polypeptides, are used, inter alia, for conferring a telomerase activity (e.g., telomerase catalytic activity, infra) in a telomerase-negative cell such as a cell from a human, a mammal, a vertebrate, or other eukaryote (see, e.g., Bodnar et al., 1998, Science 279:349 and U.S. Pat. Nos. 6,475,789 and 6,166,178). Variants that lack at least one hTRT activity (e.g., telomerase catalytic activity) are used, inter alia, to inhibit telomerase activity in a cell (e.g., by acting as "dominant negative mutants"). The hTRT variants and polynucleotides encoding them, as described herein, are similarly useful in screening assays for identifying agents that modulate telomerase activity.

The hTRT variants of the present invention are characterized by one or more deletions or mutations, relative to a naturally occurring hTRT polypeptide, in defined regions of the protein, as described in detail infra. These hTRT variants may have none, one, or several of the biological activities that may be found in naturally occurring full-length hTRT proteins. These activities include telomerase catalytic activity (the ability to extend a DNA primer that functions as a telomerase substrate by adding a partial, one, or more than one repeat of a sequence, e.g., TTAGGG, encoded by a template nucleic acid, e.g., hTR), telomerase conventional reverse transcriptase activity (see Morin, 1997, supra, and Spence et al., 1995, Science 267-988; nucleolytic activity (see Morin, 1997, supra; Collins and Grieder, 1993, Genes and Development 7; 1364; Joyce and Steitz, 1987, Trends Biochem. Sci. 12:288); primer (telomere) binding activity (see, Morin, 1997, supra; Collins et al., 1995, Cell 84:677; Harrington et al., 1995, J. Biol. Chem. 270:8893; dNTP binding activity (Morin, 1997, supra; Spence et al., supra); and RNA (e.g., hTRT) binding activity (see Morin, 1997, supra; Harrington et al., 1997, Science 275:973; Collins et. al., 1995. Cell 81:677).

In one embodiment of the invention, the hTRT variant has telomerase catalytic activity. Telomerase catalytic activity may be processive or nonprocessive. Processive telomerase catalytic activity occurs when a telomerase RNP adds multiple repeats to a primer or telomerase before, the DNA is released by the enzyme complex (see, e.g., Morin, 1989, Cell 59:521 and Morin, 1997, Eur. J. Cancer 33:750). Nonprocessive activity occurs when telomerase adds a partial, or only one, repeat to a primer and is then released (see Morin, 1997, supra). In a particular embodiment of the invention, the hTRT variant has processive telomerase catalytic activity.

Processive telomerase catalytic activity can be assayed by a variety of methods, including the "conventional assay" (Morin, 1989, Cell 59:521), the TRAP assay (U.S. Pat. No. 5,629,154; see also, PCT publication WO 97/15687, PCT publication WO 95/13381; Krupp et al. Nucleic Acids Res., 1997, 25: 919; Wright et al., 1995, Nucl. Acids Res. 23:3794), the "dot blot immunoassay" (U.S. Pat. application Ser. No. 08/833,377), and other assays (e.g., Tatematsu et al., 1996, Oncogene 13:2265). The TRAPeze™ Kit (Oncor, Inc., Gaithersburg, Md.) may be used. The telomerase substrate used in these assays may have a natural telomere sequence, or may be have a synthetic oligonucleotide with a different sequence (see, e.g., Morin, 1989, Cell 59:521; Morin, 1991, Nature 353:454-56).

As used herein, an hTRT variant is considered to have a specified activity if the activity is exhibited by either the hTRT variant polypeptide without an associated hTR RNA or in an hTRT-hTR complex. Each of the hTRT activities described supra is also described in detail in U.S. Pat. Nos. 6,475,789 and 6,166,178.

II. hTRT Variants Described a) hTRT Variants with Telomerase Catalytic Activity

It has now been demonstrated that large regions of the hTRT protein can be mutated (e.g., deleted) without loss of telomerase catalytic activity. Sites of mutation (e.g., deletion) are described herein with reference to the amino acid sequence provided in FIG. 1 and encoded in plasmid pGRN121 (ATCC accession number 209016); however it will be recognized that the same or equivalent mutations may be made in other hTRT polypeptides, e.g., naturally occurring variants such as polymorphic variants, hTRT fusion proteins, hTRT homologs (e.g., from non-human species), and the like. For ease of discussion, the residues of the full-length hTRT protein having a sequence as provided in FIG. 1 are referred to herein by number, with the amino-terminal methionine (M) in FIG. 1 numbered "1", and the carboxy-terminal aspartic acid (D) numbered "1132".

Regions of the hTRT protein that can be mutated (e.g., deleted) without abolishing telomerase catalytic activity include the regions from amino acid residues 192 to 323 (inclusive) and residues 415 to 450 (inclusive). As is demonstrated in the experiments described infra, all or part of either of these regions, or all or part of both of them, can be deleted without abolishing the telomerase catalytic activity of the protein. The regions from amino acid residues 192 to 323 and residues 415 to 450 may be referred to as "nonessential" regions of hTRT (i.e., not essential for telomerase catalytic activity). Thus, in various embodiments, the hTRT variants of the invention comprise deletions of, or other mutations in, these nonessential regions of hTRT. As described in Section IV, infra, certain mutations (e.g., deletion of residues 415-450) alter RNA-binding characteristics of the hTRT variant.

Examples of mutations that can be made in the hTRT polypeptides of the invention include deletions, insertions, substitutions, and combination of mutations. Thus, in some embodiments the mutation is a deletion of at least one, typically at least about 10, and often at least about 25, at least about 50, or at least about 100 amino acid residues relative to a naturally occurring hTRT. In alternative embodiments, the mutation is a single amino acid substitution in a "non-essential" region, or a combinations of substitutions. Substitutions may be conservative substitutions or non-conservative substitutions. In still other embodiments, the mutation is an insertion or substitution of amino acids, for example the insertion of residues that encode an epitope tag or novel proteolytic site. Substitutions may be of one or more (e.g., all) of the residues in the above-mentioned regions or may be combined with deletions so that, e.g., a shorter heterologous sequence is a substituted for a longer hTRT sequence. It will be appreciated, as noted supra, that in some embodiments the hTRT variant has more than one different type of mutation relative to a naturally occurring hTRT protein (e.g., a deletion and a point mutation).

The hTRT variants of the invention have certain advantages compared to naturally occurring hTRT proteins. In some embodiments, mutations may confer more efficient in vitro expression of active hTRT (e.g., in expression systems in which shorter polypeptides are more efficiently expressed than longer polypeptides), may provide sequences that aid in purification (e.g., an epitope tag sequence), or may add a new functional moiety to the hTRT polypeptide (e.g., a 3'→5' exonuclease domain from DNA polymerase 1).

As noted supra, the hTRT variant polypeptides of the invention comprising mutations (e.g., deletions) in the "nonessential" regions of the hTRT retain telomerase catalytic activity. These variants, and polynucleotides that encode them, are useful in any application for which other catalytically active hTRT proteins (e.g., wild-type hTRT proteins) or polynucleotides may be used, including, inter alia, in therapeutic, diagnostic, and screening uses. Exemplary uses of hTRT polypeptides and polynucleotides are described in additional detail in the afore cited U.S. Pat. Nos. 6,475,789 and 6,166,178.

In one embodiment, the hTRT variant of the invention is used to increase the proliferative capacity of a cell by, e.g., increasing telomerase activity in the cell (see, Bodnar et al. supra, and U.S. Pat. Nos. 6,475,789 and 6,166,178 for a detailed description of exemplary methods). Briefly, in one embodiment, a polynucleotide comprising (i) a sequence encoding the hTRT variant polypeptide; (ii) an operably linked promoter (e.g., a heterologous promoter); and, (iii) optionally polyadenylation and termination signals, enhancers, or other regulatory elements, is introduced into a target cell (e.g., by transfection, lipofection, electroporation, or any other suitable method) under conditions in which the hTRT variant polypeptide is expressed. The expression in the cell of the catalytically active hTRT variant of the invention results in increased proliferative capacity (e.g., an immortal phenotype).

In another embodiment, the hTRT variant is used for in vitro reconstitution (IVR) of a telomerase ribonucleoprotein (e.g., comprising the hTRT variant polypeptide and a template RNA, e.g., hTR) that has telomerase catalytic activity. In vitro reconstitution methods are described in, e.g., Weinrich et al., 1997, Nat Genet. 17:498, and U.S. Pat. Nos. 6,475,789 and 6,166,178. Briefly, in one embodiment, an expression vector encoding an hTRT variant of the invention is expressed in an in vitro expression system (e.g., a coupled transcription-translation reticulocyte lysate system such as that described in U.S. Pat. No. 5,324,637). In a particular embodiment, the hTRT variant polypeptide is coexpressed with hTR. In an alternative embodiment, the hTRT variant and hTR are separately expressed and then combined (mixed) in vitro. In the latter method, the hTR RNA and/or hTRT polypeptide may be purified before mixing. In this context, the hTRT polypeptide is "purified" when it is separated from at least one other component of the in vitro expression system, and it may be purified to homogeneity as determined by standard methods (e.g., SDS-PAGE). The in vitro reconstituted (IVR) telomerase has a variety of uses; in particular it is useful for identifying agents that modulate hTRT activity (e.g., drug screening assays).

(b) Deletion Variants Lacking Telomerase Catalytic Activity

In an other aspect, the invention provides hTRT deletion variants that lack telomerase catalytic activity (i.e., having less than 1% of the wild type activity), as well as polynucleotides encoding the variants lacking telomerase catalytic activity. In particular, the invention provides variants comprising one or more of the following deletions relative to wild-type hTRT: residues 192-450, 637-660, 638-660, 748-766, 748-764, and 1055-1071. These variants are referred to herein as "PCA$^-$ variants" (processive telomerase catalytic activity minus variants).

The PCA$^-$ variant proteins and polynucleotides of the invention lacking telomerase catalytic activity are used in, inter alia, therapeutic, screening and other applications. For example, PCA$^-$ variants are useful as dominant negative mutants for inhibition of telomerase activity in a cell. In one embodiment, a PCA$^-$ variant is introduced into a cell (e.g., by transfection with a polynucleotide expression vector expressing the PCA$^-$ variant), resulting in sequestration of a cell component (e.g., hTR) required for accurate telomere elongation. Thus, for example, administration of a polypeptide that binds hTR, a DNA primer, a telomerase-associated protein, or other cell component, but which does not have telomerase catalytic activity, is used to reduce endogenous telomerase activity in the cell or to otherwise interfere with telomere extension (e.g., by displacing active telomerase from telomeric DNA). Similarly, in certain embodiments, a PCA$^-$ variant of the invention having one or several hTRT activities (i.e., other than processive telomerase catalytic activity) is used for screening for agents that specifically modulate (inhibit or activate) a telomerase activity other than telomerase catalytic activity. The use of hTRT variants as dominant negative mutants, and in other applications, is described in detail in U.S. Pat. Nos. 6,475,789 and 6,166,178.

III. Making hTRT Variants

The hTRT variant polypeptides and polynucleotides of the invention may be produced using any of a variety of techniques known in the art. In one embodiment, a polypeptide having the desired sequence, or a polynucleotide encoding the polypeptide, is chemically synthesized (see, e.g., Roberge, et al., 1995, *Science* 269:202; Brown et al., 1979, *Meth. Enzymol.* 68:109). More often, the hTRT variant polypeptides and polynucleotides of the invention are created by manipulation of a recombinant polynucleotide encoding an hTRT polypeptide. Examples of suitable recombinant polynucleotides include pGRN121, supra, and other hTRT cDNA and genomic sequences.

Methods for cloning and manipulation of hTRT encoding nucleic acids (e.g., site-specific mutagenesis, linker scanning mutagenesis, and the like) are well known in the art and are described, for example, in Sambrook et al., 1989, MOLECULAR CLONING: A LABORATORY MANUAL, 2ND ED., VOLS. 1-3, Cold Spring Harbor Laboratory, and Ausubel et al., 1997, CURRENT PROTOCOLS IN MOLECULAR BIOLOGY, Greene Publishing and Wiley-Interscience, New York. One convenient method for producing a polynucleotide encoding a desired hTRT deletion variant is by restriction digestion and subsequent ligation of a hTRT polynucleotide, to remove a region(s) of the polynucleotide encoding the amino acid residues to be deleted. If desired, restriction sites can be introduced or removed from a synthetic or naturally occurring hTRT gene to facilitate the production and detection of variants.

Typically, the recombinant polynucleotide encoding an hTRT variant of the invention is linked to appropriate regulatory elements (e.g., promoters, enhancers, polyadenylation signals, and the like) and expressed in a cell free system (see, e.g., Weinrich et al., supra), in bacteria (e.g., E. coli), in ex vivo animal cell culture (see, e.g., Bodnar et al., supra), in animals or plants (e.g., transgenic organisms or in gene therapy applications), or by any other suitable method. Suitable expression systems are well known in the art and include those described in Weinrich et al., and Bodnar et al., both supra, and in U.S. Pat. Nos. 6,475,789 and 6,166,178.

Additional hTRT variants of the invention may be made using "DNA shuffling" in vitro recombination technology (see, e.g., Crameri et al., 1998, Nature 391:288-291; Patten et al., 1997, Curr. Opin. BiotechnoL 8:724-733, Stemmer, 1994, Nature 370:389-391; Crameri et al., 1996, Nature Medicine, 2:1-3; Crameri et al., 1996, Nature Biotechnology 14:315-319; WO 95/22625; Stemmer, 1995, Science 270:1510; Stemmer et al., 1995, Gene, 164, 49-53; Stemmer, 1995, Bio/technology, 13:549-553; Stemmer, 1994, Proc. Natl. Acad. Sci. USA 91:10747-10751). The specific deletion variants described supra, "wild-type hTRT" and non-human hTRT-homologs may be used in individually or various combinations as starting substrates to produce novel polypeptides with the desired activity. The activity or activities of the resulting polypeptides determined using the assays described in Section I, supra.

U.S. Pat. No. 6,166,178 refers to methods, reagents, vectors, and cells useful for expression of hTRT polypeptides and nucleic acids. In one embodiment, expression of the hTRT protein, or fragment thereof, comprises inserting the coding sequence into an appropriate expression vector (i.e., a vector that contains the necessary elements for the transcription and translation of the inserted coding sequence required for the expression system employed). For mammalian host cells, viral-based and nonviral expression systems are provided. Nonviral vectors and systems include plasmids and episomal vectors. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV).

For the production of anti-hTRT antibodies, hosts such as goats, sheep, cows, guinea pigs, rabbits, rats, or mice, may be immunized by injection with hTRT protein or any portion, fragment, or oligopeptide thereof that retains immunogenic properties. In selecting hTRT polypeptides for antibody induction, one need not retain biological activity; however, the protein fragment, or oligopeptide must be immunogenic. Immunogenicity can be determined by injecting a polypeptide and adjuvant into an animal (e.g., a rabbit) and assaying for the appearance of antibodies directed against the injected polypeptide (Harlow and Lane, Antibodies: A Laboratory Manual, Cold Spring Harbor Laboratory, New York, 1988).

Peptides used to induce specific antibodies typically have an amino acid sequence consisting of at least five amino acids, preferably at least 8 amino acids, more preferably at least 10 amino acids. Usually they will mimic or have substantial sequence identity to all or a contiguous portion of the amino acid sequence of the protein of SEQ ID NO:2. Depending on the host species, various adjuvants may be used to increase immunological response. Immunogenic peptides or polypeptides having an hTRT sequence can be used to elicit an anti-hTRT immune response in a patient (i.e., act as a vaccine). An immune response can also be raised by delivery of plasmid vectors encoding the polypeptide of interest. Further details on techniques for formulation and administration may be found in the latest edition of Remington's Pharmaceutical Sciences, Maack Publishing CO., Easton Pa.

IV. Exemplary hTRT Variants a) Generally

Exemplary hTRT variants were created by in vitro mutagenesis of polynucleotides encoding a full-length hTRT protein using the method of Perez et al., 1994, J. Biol. Chem. 269:22485-87. The mutant polynucleotides were expressed in vitro and telomerase reconstituted by in vitro mixing of hTRT and human telomerase RNA as described in Weinrich et al., 1997, supra. Reconstitution reactions were carried out using 0.5 pmole, 20 pmole, and, in some cases, other amounts of added hTR. Telomerase processive catalytic activity was assayed using a modified TRAP assay (Weinrich et al., 1997, supra). The results are summarized in Table 1.

TABLE 1

| Deletion Name | Oligo | Amino acids deleted | Activity[1] |
|---|---|---|---|
| pGRN234 | RT1 + RT2 | none (delete NcoI site) | + |
| pGRN226 | RT3A | 192–323 | + |
| RT3 | RT3 | 200–326 | + |
| pGRN237 | RT4A | 192–271 | + |
| RT4 | RT4 | 200–271 | + |
| pGRN210 | LM122-Nuc | 222–240 | + |
| pGRN235 | RT5 | 415–450 | + |
| pGRN242 | RT3A + RT5 | 192–326 + 415–450 | + |
| pGRN243 | RT4A + RT5 | 192–271 + 415–450 | + |
| pGRN240 | RT3A/5 | 192–450 | − |
| pGRN238 | RT6A | 637–660 | − |
| RT6 | RT 6 | 638–660 | − |
| pGRN239 | RT8A | 748–766 | − |
| RT8 | RT8 | 748–764 | − |
| pGRN241 | RT10 | 1055–1071 | − |
| pGRN236 | RT11 | 1084–1116 | − |
| pGRN209 | LM121-WG | 930–934 | − |
| pGRN231 | | 560–565 | − |

"+" = at least 40% activity compared to in vitro reconsitution using wild-type hTRT (e.g., encoded by pGRN125; see Weinrich et al., 1997, supra)
"−" = less than 1% activity.

Certain of the hTRT variants described supra are altered in their ability to bind hTR. The variants encoded by pGRN235, pGRN242 and pGRN243 exhibited telomerase activity when 20 pmoles hTR (template RNA) was included in the reconstitution reaction, but showed a low or undetectable level of activity when 0.5 pmoles of hTR was used. The variable activity of these variants indicates that these variants have altered (e.g., decreased) hTR binding activity. Thus, the region from 415 to 450 is likely involved in RNA binding (e.g., by affecting the conformation of the protein).

This result suggests that the region immediately upstream of residue 415, corresponding to the conserved "CP" domain (Bryan et al., 1998, *Proc. Nat'l. Acad. Sci.* 95:8479-8484) is a region of contact between the hTRT protein and hTR (e.g., corresponding to about residues 405 to 418 as set forth in FIG. 1). This conclusion is supported by the relative lack of conservation of sequence when human and mouse TRT sequences are compared in the region corresponding to hTRT residues 415-450.

hTR binding to hTRT was also affected by mutations and deletions in the region 560-565. RNA binding was assayed by adding purified hTR to epitope tagged TRT proteins (i.e., including a FLAG sequence; Immunex Corp, Seattle Wash.). The hTR and protein were incubated under conditions under which tagged "wild-type" hTRT associates with template RNA (hTR), and the hTRT protein or hTRT-hTR complex (if present) were immunoprecipitated. The precipitated complex was assayed for the presence and amount of associated RNA. Deletion of residues 560-565 dramatically decreased the binding of hTR by hTRT, with the concurrent expected decrease in telomerase activity (see Table 1, pGRN231). Mutation of phenylalanine (F) to alanine (A) mutation at position 561 of hTRT (the "F561A" variant; see, Weinrich et al., 1997, supra) resulted in reduced binding of hTR: this variant did not effectively bind hTR in association reactions when hTR was present at 0.5 pmoles, and showed less-than wild-type binding at 20 pmoles hTR. Mutation of tyrosine at 562 to alanine similarly resulted in a loss of hTR binding activity (e.g., about a 70-80% reduction compared to the wild-type sequence). Mutation of threonine at position 564 to alanine resulted in a decrease in RNA binding by approximately 20% compared to wild-type. In contrast, mutation of residues 560 (F) and 565 (E) to alanine did not affect hTR binding. These results indicate that the region from 560-565 is involved in RNA binding, e.g., by providing residues that contact hTR.

As will be apparent to one of skill advised of these results, the telomerase reconstitution may be inhibited using peptides comprising the sequence corresponding the hTRT residues 405-418, 560-565, or fragments thereof, or peptide mimetics of such sequences. Thus, in one embodiment of the present invention, telomerase activity in a cell or an in vitro composition in which TRT protein and TR RNA are present, such as a telomerase reconstitution assay, is reduced by introducing to the cell or in vitro composition a polypeptide comprising the sequence FFYVTE (SEQ ID NO:3), a polypeptide comprising the sequence YGVLLKTHCPLRAA (SEQ ID NO:4), a polypeptide consisting essentially of FFYVTE (SEQ ID NO:3), a polypeptide consisting essentially of FYVT (SEQ ID NO:5), a polypeptide consisting essentially of YGVLLK-THCPLRAA (SEQ ID NO:4), a fragment of at least three residues of the aforementioned polypeptides, or a peptide analog or mimetic of the polypeptide of any of the aforementioned compositions.

Peptide mimetics (or peptide analogs) are well known and are commonly used in the pharmaceutical industry as non-peptide drugs with properties analogous to those of the template polypeptide (Fauchere, 1986, *Adv. Drug Res.* 15:29; Veber et al., 1985, *TINS* p.392; and Evans et al., 1987, *J. Med. Chem.* 30:1229). Generally, peptidomimetics are structurally similar to the paradigm polypeptide having the sequence from hTRT but have one or more peptide linkages optionally replaced by a linkage selected from the group consisting of: —$CH_2NH$—, —$CH_2S$—, —$CH_2$—$CH_2$—, —CH'CH— (cis and trans), —$COCH_2$—, —$CH(OH)CH_2$—, and —$CH_2SO$—. Peptide mimetics may have significant advantages over polypeptide embodiments of this invention, including, for example: more economical production, greater chemical stability, enhanced pharmacological properties (half-life, absorption, potency, efficacy, etc.), altered specificity (e.g., a broad-spectrum of biological activities), reduced antigenicity, and others. In addition to modifications to the peptide backbone, synthetic or non-naturally occurring amino acids can also be used to substitute for the amino acids present in the polypeptide or in the functional moiety of fusion proteins. Synthetic or non-naturally occurring amino acids refer to amino acids which do not naturally occur in vivo but which, nevertheless, can be incorporated into the peptide structures described herein. Preferred synthetic amino acids are the d-α-amino acids of naturally occurring l-α-amino acid, mentioned above, as well as non-naturally occurring d- and l-α-amino acids represented by the formula H2NCHR5COOH where R5 is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5) -alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —C(O)R2 where R2 is selected from the group consisting of hydrogen, hydroxy, lower alkyl, lower alkoxy, and —NR3R4 where R3 and R4 are independently selected from the group consisting of hydrogen and lower alkyl, (g) —S(O)nR6 where n is an integer from 1 to 2 and R6 is lower alkyl and with the proviso that R5 does not define a side chain of a naturally occurring amino acid. Other preferred synthetic amino acids include amino acids wherein the amino group is separated from the carboxyl group by more than one carbon atom such as β-alanine, γ-aminobutyric acid, and the like.

It will also be recognized by those of skill upon reviewing these results that the compositions (e.g., polypeptides and mimetics) described supra can be used to identify telomerase association and activity inhibitors other than the disclosed polypeptide and mimetics. These compositions may be used, for example, in rational drug design for e.g., computer modeling of telomerase activity modulators (e.g., modulators that inhibit the association of TRT and TR or that catalyze the disassociation of the telomerase complex), as positive controls in screens for modulators of telomerase activity, or in competition assays with candidate telomerase activity modulators.

b) Methods

Mutagenesis of the hTRT coding sequence of pGRN125 was carried out using the methods described by Perez et al., 1994, *J. Biol. Chem.* 269:22485-87. Most of the deletion mutants were generated from the plasmid pGRN125 (Weinrich et al., 1997, supra). Deletion mutants pGRN235 and pGRN236 were made in a secondary round of mutagenesis in an altered pGRN234. pGRN234 was generated by mutating (deleting) the Nco I site in pGRN125 (changing CAC to CAT in the histidine residue at position 754) and introducing a new NcoI site at the translation start site (ATG). Table 2 shows exemplary oligonucleotides used to generate the plasmids expressing the deletion variants of the invention.

TABLE 2

| Oligo Name | Oligo sequence 5'-3' | length | Description | SEQ ID NO: |
|---|---|---|---|---|
| RT1 | GAAGGCCGCCCACGGGCACGTCCGC | 25 | Mutagenesis oligo to delete Nco I site from pGRN125 | 6 |
| RT2 | CCCGGCCACCCCAGCCATGGCGCGC GCTCCCC | | Mutagenesis oligo to create Nco I site @ ATG of pGRN 125 | |
| RT5 | TACGGGGTGCTCCTCAAGACGCACT GCCCGCTGCTCCGCCAGCACAGCAG CCCCTGGCAG | 60 | Mutagenesis oligo to create a deletion of aa 415-450 in pGRN125 | 8 |
| RT10 | TACTCCATCCTGAAAGCCAAGAACG CAGGGCTGTGCCACCAAGCATTCCT GCTCAAGCTG | 60 | Mutagenesis oligo to create a deletion of aa 1055-1071 in pGRN125 | 9 |
| RT11 | CTGTGCCACCAAGCATTCCTGCTCA AGCTGGCCGCAGCCAACCCGGCACT GCCCTCAGAC | 60 | Mutagenesis oligo to create a deletion of aa 1083-1116 in pGRN125. Oligo creates a NheI site. | 10 |
| RT3A | ACTCAGGCCCGGCCCCCGCCACACG CTAGCGAGACCAAGCACTTCCTCTA CTCCTCAGGC | 60 | Mutagenesis oligo to create a deletion of aa 192-323 in pGRN125. Oligo creates a NheI site. | 11 |
| RT4A | ACTCAGGCCCGGCCCCCGCCACACG CTAGCGTGGTGTCACCTGCCAGACC CGCCGAAGAA | 60 | Mutagenesis oligo to create a deletion of aa 192-271 in pGRN125. Oligo creates a NheI site. | 12 |
| RT6A | ATCCCCAAGCCTGACGGGCTGCGGC CGATTGTTAACATGCTGTTCAGCGT GCTCAACTACGAGCGGGCG | 69 | Mutagenesis oligo to create a deletion of aa 638-660 in pGRN125. Oligo creates a Hpa I site. | 13 |
| RT8A | ACGTACTGCGTGCGTCGGTATGCCG TGGTCACAGATCTCCAGCCGTACAT GCGACAGTTCGTG | 63 | Mutagenesis oligo to create a deletion of aa 748-766 in pGRN125. Oligo creates a BgI II site. | 14 |
| RT3A/5 | ACTCAGGCCCGGCCCCCGCCACACG CTAGCCTGCTCCGCCAGCACAGCAG CCCCTGGCAG | 60 | Mutagenesis oligo to create a deletion of aa 192-450 in pGRN125. Oligo creates a NheI site. | 15 |
| LM121-WG | GTTCAGATGCCGGCCCACGGCCTAT TCCCTCTAGATACCCGGACCCTGGA GGTGCAGAGCGAC | 63 | Mutagenesis oligo to delete aa 930-934. Oligo introduces a new XbaI site | 16 |
| LM122-Nuc | CCCTGGGCCTGCCAGCCCCGGGTGC CGGCGCTGCCCCTGAGCCGGAGCGG | 50 | Mutagenesis oligo to delete aa 222-240. Oligo introduces a new Nae I site | 17 |
| RT3 | GCTAGTGGACCCCGAAGGCGTCTGG GATGCGAGACCAAGCACTTCCTCTA CTCCTCAGGC | 60 | Mutagenesis oligo to create a deletion of aa 200-323 in pGRN125 | 18 |
| RT4 | GCTAGTGGACCCCGAAGGCGTCTGG GATGCGTGGTGTCACCTGCCAGACC CGCCGAAGAA | 60 | Mutagenesis oligo to create a deletion of aa 200-271 in pGRN125 | 19 |
| RT6 | GACGGGCTGCGGCCGATTGTGAACA TGGACCTGTTCAGCGTGCTCAACTA CGAGCGGGCG | 60 | Mutagenesis oligo to create a deletion of aa 638-660 in pGRN125 | 20 |
| RT8 | ACGTACTGCGTGCGTCGGTATGCCG TGGTCACCTTGACAGACCTCCAGCC GTACATGCGA | 60 | Mutagenesis oligo to create a deletion of aa 748-764 in pGRN125 | 21 |

V. Definitions

The following terms are defined infra to provide additional guidance to one of skill in the practice of the invention:

When comparing regions between a first and second polypeptide, sequences can be aligned by inspection (e.g., alignment of identical sequences) or by computer implemented alignment of the two sequences. Thus, for example, the residues 192 to 323 of the hTRT polypeptide having the sequence set forth in FIG. 1 "correspond" to residues in the same position in a hTRT polypeptide that differs from the FIG. 1 sequence due to polymorphic variation, or other mutations or deletions (e.g., when the two polypeptides are optimally aligned). Alignments may also be carried out using the GAP computer program, version 6.0 (Devereux et al, 1984, Nucl. Acid. Res. 12:387; available from the University of Wisconsin Genetics Computer Group, Madison, Wis.). The GAP program utilizes the alignment method of Needleham and Wunsch, 1970 J. Mol. Biol. 48: 443-453 as revised by Smith and Waterman, 1981, Adv. Appl. Math 2:482. The preferred default parameters for the GAP program include (1) the weighted comparison matrix of Gribskov and Burgess, 1986, Nucl. Acid. Res. 14:6745 as described by Schwartz and Dayhoff, eds., 1979, ATLAS OF PROTEIN SEQUENCE AND STRUCTURE, National Biomedical Research Foundation, pp. 353-358 (2) a penalty of 3.0 for each gap and an additional 0.10 penalty for each symbol in each gap; and (3) no penalty for end gaps. Alternatively, alignments can be carried out using the BLAST algorithm, which is described in Altschul et al., 1990, J. Mol. Biol. 215:403-410 using as defaults a wordlength (W) of 11, the BLOSUM62 scoring matrix (see Henikoff & Henikoff, 1989, Proc. Natl. Acad. Sci. USA 89:10915); alignments (B) of 50, expectation (E) of 10, M=5, and N=−4. A modification of BLAST, the "Gapped BLAST" allows gaps to be introduced into the alignments that are returned (Altschul et al., 1997, Nucleic Acids Res 1:3389-3402). Software for performing BLAST analyses is publicly available through the internet website of the National Center for Biotechnology Information.

As used herein, "stringent hybridization conditions" or "stringency" refers to conditions in a range from about 5° C. to about 20° C. or 25° C. below the melting temperature ($T_m$) of the target sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) *Methods In Enzymology*, Vol. 152: *Guide To Molecular Cloning Techniques*, San Diego: Academic Press, Inc. and Sambrook et al. (1989) *Molecular Cloning: A Laboratory Manual,* 2ND ED., VOLS. 1-3, Cold Spring Harbor Laboratory hereinafter, "Sambrook", both incorporated herein by reference). As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization in *Nucleic Acid Hybridization* (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, e.g., Sambrook, supra and Ausubel et al. supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed.

As used herein, the term "substantial identity," "substantial sequence identity," or "substantial similarity" in the context of nucleic acids, refers to a measure of sequence similarity between two polynucleotides. Substantial sequence identity can be determined by hybridization under stringent conditions, by direct comparison, or other means. For example, two polynucleotides can be identified as having substantial sequence identity if they are capable of specifically hybridizing to each other under stringent hybridization conditions. Other degrees of sequence identity (e.g., less than "substantial") can be characterized by hybridization under different conditions of stringency. Alternatively, substantial sequence identity can be described as a percentage identity between two nucleotide (or polypeptide) sequences. Two sequences are considered substantially identical when they are at least about 60% identical, preferably at least about 70% identical, or at least about 80% identical, or at least about 90% identical, or at least about 95% or 98% to 100% identical. Percentage sequence (nucleotide or amino acid) identity is typically calculated by determining the optimal alignment between two sequences and comparing the two sequences. For example an exogenous transcript used for protein expression can be described as having a certain percentage of identity or similarity compared to a reference sequence (e.g., the corresponding endogenous sequence). Optimal alignment of sequences may be conducted using the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. U.S.A. 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection. The best alignment (i.e., resulting in the highest percentage of identity) generated by the various methods is selected. Typically these algorithms compare the two sequences over a "comparison window" (usually at least 18 nucleotides in length) to identify and compare local regions of sequence similarity, thus allowing for small additions or deletions (i.e., gaps). Additions and deletions are typically 20 percent or less of the length of the sequence relative to the reference sequence, which does not comprise additions or deletions. It is sometimes desirable to describe sequence identity between two sequences in reference to a particular length or region (e.g., two sequences may be described as having at least 95% identity over a length of at least 500 basepairs). Usually the length will be at least about 50, 100, 200, 300, 400, or 500 basepairs, amino acids, or other residues. The percentage of sequence identity is calculated by comparing two optimally aligned sequences over the region of comparison, determining the number of positions at which the identical nucleic acid base (e.g., A, T, C, G, or U) occurs in both sequences to yield the number of matched positions, and determining the number (or percentage) of matched positions as compared to the total number of bases in the reference sequence or region of comparison.

When referring to an "activity" of an hTRT variant, a variant is considered to be active in an assay of it displays at least 40% of the activity characteristic of the hTRT polypeptide having the sequence set forth in FIG. 1 ("wild type"). A variant is considered to lack activity when it has less that 1% of the "wild type" activity. A variant with greater than 1% activity and less than 40% activity has "intermediate activity."

As used herein, "conservative substitution," refers to substitution of amino acids with other amino acids having similar properties (e.g., acidic, basic, positively or negatively charged, polar or non-polar). The following six groups each contain amino acids that are conservative substitutions for one another: 1) alanine (A), serine (S), threonine (T); 2) aspartic acid (D), glutamic acid (E); 3) asparagine (N), glutamine (Q); 4) arginine (R), lysine (K); 5) isoleucine (I), leucine (L), methionine (M), valine (V); and 6) phenylalanine (F), tyrosine (Y), tryptophan (W) (see also, Creighton, 1984, PROTEINS, W. H. Freeman and Company).

All publications and patent documents cited in this application are incorporated by reference in their entirety and for all purposes to the same extent as if each individual publication or patent document were so individually denoted.

The invention claimed is:

1. An isolated nucleic acid that encodes a polypeptide having at least 90% sequence identity to SEQ ID NO:2 and wherein said polypeptide comprises one or more deletions selected from the group consisting of:
   a) all of amino acid residues 930-934;
   b) at least 10 consecutive amino acids from residues 637-660;
   c) at least 10 consecutive amino acids from residues 748-766;
   d) at least 10 consecutive amino acids from residues 1055-1071; and
   e) at least 10 consecutive amino acids from residues 1084-1116;

wherein said polypeptide lacks processive telomerase enzyme activity
and wherein said polypeptide inhibits telomerase catalytic activity when expressed in a cell expressing human telomerase reverse transcriptase (hTRT) and human telomerase RNA component.

2. The isolated nucleic acid of claim 1 that encodes a polypeptide that has at least 95% sequence identity to SEQ ID NO:2.

3. The nucleic acid of claim 1 wherein said nucleic acid encodes a polypeptide comprising one or more deletions selected from the group consisting of residues 637-660, 748-766, 1055-1071, and 1084-1116 of SEQ ID NO:2.

4. An isolated nucleic acid that encodes a polypeptide having at least 90% sequence identity to SEQ ID NO:2 and wherein said polypeptide comprises one or more deletions selected from the group consisting of:
   a) all of amino acid residues 930-934;
   b) at least 10 consecutive amino acids from residues 637-660;
   c) at least 10 consecutive amino acids from residues 748-766;
   d) at least 10 consecutive amino acids from residues 1055-1071; and
   e) at least 10 consecutive amino acids from residues 1084-1116;

wherein said polypeptide lacks processive telomerase enzyme activity
and wherein said polypeptide:
   (a) binds a human telomerase RNA component; or
   (b) binds human telomeres.

5. The nucleic acid of claim 4, wherein said nucleic acid encodes a polypeptide that binds a human telomerase RNA component.

6. The nucleic acid of claim 4, wherein said nucleic acid encodes a polypeptide that binds human telomeres.

7. An expression vector comprising the nucleic acid of any one of claim 1 or 4.

8. The expression vector of claim 7, which is an adenovirus expression vector.

9. The isolated nucleic acid of claim 4, that encodes a polypeptide having at least 95% sequence identity to SEQ ID NO:2.

* * * * *